US007326555B2

(12) United States Patent
Konz, Jr. et al.

(10) Patent No.: US 7,326,555 B2
(45) Date of Patent: Feb. 5, 2008

(54) METHODS OF ADENOVIRUS PURIFICATION

(75) Inventors: John O. Konz, Jr., Erdenheim, PA (US); Ann L. Lee, Lansdale, PA (US); Chi Shung Brian To, North Wales, PA (US); Aaron R Goerke, Schwenksville, PA (US)

(73) Assignee: Merck & Co., Inc., Rahway, NJ (US)

( * ) Notice: Subject to any disclaimer, the term of this patent is extended or adjusted under 35 U.S.C. 154(b) by 196 days.

(21) Appl. No.: 10/512,779

(22) PCT Filed: May 13, 2003

(86) PCT No.: PCT/US03/15061

§ 371 (c)(1),
(2), (4) Date: Oct. 25, 2004

(87) PCT Pub. No.: WO03/097797

PCT Pub. Date: Nov. 27, 2003

(65) Prior Publication Data

US 2005/0153420 A1  Jul. 14, 2005

Related U.S. Application Data

(60) Provisional application No. 60/380,322, filed on May 14, 2002.

(51) Int. Cl.
C12N 7/02 (2006.01)
A61K 39/235 (2006.01)
(52) U.S. Cl. .................................. 435/239; 424/233.1
(58) Field of Classification Search ..................... None
See application file for complete search history.

(56) References Cited

U.S. PATENT DOCUMENTS

| 4,064,232 A | 12/1977 | Bachmayer et al. |
| 5,837,520 A | 11/1998 | Shabram et al. |
| 6,194,191 B1* | 2/2001 | Zhang et al. ............... 435/239 |
| 6,194,192 B1 | 2/2001 | Ueno et al. |
| 6,261,823 B1 | 7/2001 | Tang et al. |

FOREIGN PATENT DOCUMENTS

| WO | WO96/27677 | 9/1996 |
| WO | WO98/22588 | 5/1998 |
| WO | WO 01/02607 A1 | 1/2001 |
| WO | WO 01/66137 A1 | 9/2001 |
| WO | WO02/18550 A1 | 3/2002 |
| WO | WO 02/22080 A2 | 3/2002 |

OTHER PUBLICATIONS

Lander et al. Biotechnology and Bioengineering, 2002, 79(7):776-784.*

Klemperer H.G. et al., "Study of Adenovirus Antigens Fractionated by Chromatography on DEAE-Cellulose", Virology, vol. 9, pp. 536-545, 1959.

Philipson, L., "Separation on DEAE Cellulose of Components Associated with Adenovirus Reproduction", Virology, vol. 10, pp. 459-465, 1960.

Haruna et al., "Separation of Adenovirus by Chromatography on DEAE-Cellulose", Virology, vol. 13, pp. 264-267, 1961.

Huyghe B. G. et al., "Purification of a Type 5 Recombinant Adenovirus Encoding Human p53 by Column Chromatography", Human Gene Therapy, vol. 6, pp. 1403-1416, Nov. 1995.

Shabram P.W. et al., "Analytical Anion-Exchange HPLC of Recombinant Type-5 Adenoviral Particles", Human Gene Therapy, vol. 453-465, Mar. 1997.

Bett A.J. et al., "An Efficient and flexible system for construction of adenovirus vectors with insertions or deletions in early regions 1 and 3", Proc. Natl. Acad. Sci. USA, vol. 91, pp. 8802-8806, Sep. 1994.

Chroboczek J. et al., "The Sequence of the Genome of Adenovirus Type 5 and Its Comparison with the Genome of Adenovirus Type 2", Virgology, vol. 186, pp. 280-285, 1992.

Fallaux F.J. et al., "Characterization of 911: A New Helper Cell Line for the Titration and Propagation of early Region 1-Deleted Adenoviral Vectors", Human Gene Therapy, vol. 7, pp. 215-222, Jan. 1996.

Schiedner G. et al., "Efficient Transformation of Primary Human Aminiocytes by E1 Functions of Ad5: Generation of New Cell Lines for Adenoviral Vector Production", Human Gene Therapy, vol. 11, pp. 2105-2116, Oct. 2000.

Imler J.L. et al., "Novel complementation cell lines derived from human lung carcinoma A549 cells support the growth of E1-deleted adenovirus vectors", Gene Therapy, vol. 3, pp. 75-84, 1996.

Gao G.P. et al., "A Cell Line for High-Yield Production of E1-Deleted Adenovirus Vectors without the Emergence of Replication-Competent Virus", Human Gene Therapy, vol. 11, pp. 213-219, Jan. 2000.

Lander R.J., et al. "Fractional Precipitation of Plasmid DNA from Lysate by CTAB", Biotechnology and Bioengineering, vol. 79, No. 7, pp. 776-784, Sep. 30, 2002.

* cited by examiner

Primary Examiner—Stacy B. Chen
(74) Attorney, Agent, or Firm—Alysia A. Finnegan; Sheldon O. Heber

(57) ABSTRACT

A process for purifying virus particles, especially recombinant adenovirus vector particles, is presented. The process relies on various combinations of cell lysis, detergent-based precipitation of host cell contaminants away from the virus, depth filtration or centrifugation, ultrafiltration, nuclease digestion and chromatography to robustly and economically produce highly purified product. This process results in contaminating DNA levels which are consistently below detectable levels.

20 Claims, 10 Drawing Sheets

A. Feed

B. Flowthrough

C. Product Pool (eluate)

METHODS OF ADENOVIRUS PURIFICATION

CROSS-REFERENCE TO RELATED APPLICATIONS

This application claims benefit, under 35 U.S.C. § 119(e), to U.S. provisional application 60/380,322, filed May 14, 2002, and is a 371 of PCT/US03/15061, filed May 13, 2003.

STATEMENT REGARDING FEDERALLY-SPONSORED R&D

Not Applicable

REFERENCE TO MICROFICHE APPENDIX

Not Applicable

FIELD OF THE INVENTION

The present invention relates to methods of purifying virus particles, especially recombinant adenovirus vector particles. This process is developed to purify adenovirus from cell lysate. It uses a combination of selective precipitation, depth filtration and/or centrifugation, ultrafiltration, nuclease digestion and chromatography to robustly and economically produce highly purified product. In this process, contaminating host cell DNA levels are consistently reduced to less than the limit-of-quantitation of a PCR-based assay specific for human DNA ($<5$ pg/$10^{11}$ vp).

BACKGROUND OF THE INVENTION

Advances in the areas of the use of recombinant viral vectors for gene therapy and DNA vaccination applications have created a need for large scale manufacture and purification of clinical-grade virus. One such family of viruses are the adenoviruses. The adenoviruses are grouped within the family Adenoviridae, which are split into the genus *Aviadenovirus* (birds) and *Mastadenovirus* (human, simian, bovine, equine, porcine, ovine, canine and opossum). A review of the family Adenoviridae can be found in Fundamental Biology, $3^{rd}$ Ed., Fields, B. N., Knipe, D. M., and Howley, P. M., Ed., at Chapter 30, pp. 979-1016 (1996), which is hereby incorporated by reference. Of specific interest in gene vaccination and/or gene therapy applications is the use of a first generation (FG) replication incompetent adenovirus, crippled by E1 and/or E1/E3 gene deletions, based on serotype 5 of adenovirus. Adenovirus has a broad cell tropism including professional antigen presenting cells such as macrophages and dendritic cells, can infect (if not replicate in) cells from most animal species, and can be produced in large quantities in appropriate human cell lines designed to provide the E1 gene product in trans. The adenovirus genome is generally associated with benign pathologies in humans, and the genomic organization of the virus has been well studied since its discovery in the early 1950s. In addition, the genome is amenable to manipulation, depending on the strategy utilized to construct the respective vector. A replication-incompetent virus (such as an E1/E3 deleted Ad5gag vector expressing a HIV gag transgene, as exemplified herein) requires a cell line which complements the deletions. Any such cell line may be used to generate recombinant virus vectors, with preferred, but not limiting, cell lines including 293 cells and PER.C6™ cells. To this end, numerous $1^{st}$ generation recombinant adenovirus vectors have been described in the literature (e.g., see Bett, et al., 1994, *Proc. Natl. Acad. Sci.* 91:8802-8806; WO 01/02607 and WO 02/22080). "Gutless" adenoviral vectors are a $2^{nd}$ generation adenoviral vector generally devoid of viral protein-coding sequences, frequently with viral proteins supplemented in trans by a helper virus (often an E1-deleted adenovirus) grown with the helper-dependent (HD) adenovector in a packaging cell line (e.g., PER.C6™). Absent viral proteins, these viral vectors can, in the alternative, be supplemented in trans by a cell line and/or "helper virus" capable of expressing the structural and functional adenoviral proteins necessary for successful replication, packaging and rescue. In view of the increased popularity of these viral vectors and the ultimate need to prepare commercial scale quantities of either a viral based vaccine or gene therapy vehicle, it has become essential to devise economical and scalable methods of production and purification.

Early reports of small scale chromatographic purification of adenovirus were reported in the late 1950s and early 1960s (e.g., see Klemperer and Pereira 1959, *Virology* 9: 536-545; Philipson, 1960, *Virology* 10: 459-465; Haruna, et al., 1961, *Virology:* 13 264-267), but was replaced by centrifugation in a CsCl gradient. In the last decade chromatographic purification of adenovirus has again been reported.

U.S. Pat. No. 5,837,520 (see also Huyghe et al., 1995, *Human Gene Therapy* 6: 1403-1416) disclose a method of purifying adenovirus which comprises treating the cell lysate with a nuclease, followed by (1) anion exchange and (2) metal ion chromatography.

U.S. Pat. No. 6,261,823 discloses a method of purifying adenovirus which comprises subjecting a virus preparation to anion exchange chromatography followed by size exclusion chromatography.

U.S. Pat. No. 6,194,191 discloses methods of purifying adenovirus using low perfusion rates during cell culture, a detergent lysis step, and/or a single chromatography step.

Shabram et al., 1997 (*Human Gene Therapy* 8: 453-465) discloses a method for measuring Ad5 concentration with analytical anion exchange chromatography.

Despite these reports and others, there remains a need for the development of a large scale process for purification of viral vectors generated within host cell culture systems which address both quantitative and qualitative issues that are imposed upon a commercialized vaccine or gene therapy product. The present invention addresses and meets these needs by disclosing a purification process which, in part, relies upon a selective precipitation step which facilitates removal of vast quantities of contaminating/impure DNA by clarification.

SUMMARY OF THE INVENTION

The present invention relates to methods of purifying virus particles. To this end, the present invention relates to methods of purifying virus particles from a cell lysate which comprises selectively precipitating impurity nucleic acid (DNA) molecules away from the virus particles within the post-lysis host cell culture medium by adding a selective precipitation agent such that at least about 80% of host cell nucleic acid molecules are precipitated away from medium containing the virus particles. As disclosed herein, this initial step allows for the selective precipitation of impurity DNA, such as host cell DNA, with at least an 80% reduction in contaminating DNA, and as exemplified herein, even at least an 80% reduction up to about a 90% reduction in impurity DNA following clarification. A preferred virus for purification by the methods disclosed herein is any serotype of adenovirus. The adenovirus serotype to be purified is either a wild type, modified or recombinant form of the respective adenovirus serotype. The present invention is exemplified, but by no means, limited to, a method for purifying recombinant adenovirus 5 vector particles, adenovirus 6 vector particles and adenovirus 35 vector particles. Other preferred adenovirus particles for purification by the methods disclosed herein include, but are not limited to, adenovirus 26 particles and adenovirus 36 particles.

The present invention relates in part to a preferred step in the purification process, namely the inclusion of a post-lysis selective precipitation step via addition of a at least one selective precipitation agent(s) (including but not limited to a cationic detergent) which, when preferably coupled with clarification, results in removal of residual nucleic acids and other cellular debris which may also include empty viral capsids. The methodology disclosed herein results in a more robust and economically feasible method for preparing large, commercial grade quantities of highly purified adenovirus particles. Residual host cell DNA levels are consistently reduced to less than the limit-of-quantitation of a Q-PCR-based assay ($<5$ pg/$10^{11}$ vp). As disclosed herein, a reference to a "post-lysis selective precipitation step", "selective precipitation step", "selective precipitation" or the like is mean to refer to a precipitation step wherein a selective precipitation agent (SPA) is added to a certain concentration range in the preparation, causing a high percentage of contaminating nucleic acid molecules (e.g., DNA) to be selectively precipitated away from the respective virus.

The process of the present invention includes, but does not necessarily require the following process steps: (1) releasing virus particles from infected cells by a lysis step such as a detergent lysis step; (2) selective precipitation to remove a high percentage of contaminating nucleic acids; (3) depth filtration and/or centrifugation to remove cell debris and nucleic acid precipitate; (4) ultrafiltration to reduce volume and exchange buffer; (5) nuclease treatment to digest remaining nucleic acids and facilitate removal; (6) anion exchange chromatography to purify virus away from cellular contaminants, unassembled virus components and empty capsids; (7) tangential flow ultrafiltration to further remove contaminants as well as introducing a formulation buffer; (8) sterile filtration of the virus preparation; (9) optionally, including an additional step(s) to further purify the viral preparation, such as a flow-through cationic exchange chromatography step, a reversed-phase adsorption step, and/or a hydroxyapatite chromatography step; and (10) optionally, a step prior to or in conjunction with anion exchange chromatography which is a filtration step to remove particulates prior to loading on to the anion exchange chromatography column. Table 1 outlines an exemplified, step by step AdV purification process.

The present invention relates to a process for purifying wild type or recombinant virus, especially wild type or recombinant adenovirus, wherein one or more steps of the exemplified procedure (see Table 1) are omitted. Such an omission may be utilized by the artisan on a mix and match basis in order to generate a complete protocol for purification of adenovirus which is qualitatively acceptable and is formulated at a concentration amenable to clinical and/or commercial applications. Any such modified procedure preferably, but does not necessarily, include at least the following steps: (1) cell lysis; (2) a post-lysis selective DNA precipitation; (3) clarification of the remaining virus-containing supernatant, such as by depth filtration to remove cell debris and additional nucleic acid precipitate; and, (4) an ultrafiltration step to concentrate the purified virus to levels useful for clinical and/or commercial administrations and/or exchange the virus into an appropriate buffer.

Another embodiment of the present invention relates to incorporating the four steps described above, namely (1) cell lysis; (2) selective DNA precipitation; (3) clarification; (4) a concentration step (with or without a nuclease treatment); with the additional step of (5), which is an anion exchange chromatography step, in any reasonable order that results in the recovery of commercial grade quantities of adenovirus.

The present invention further relates to incorporation of additional downstream methodology beyond steps 1-5 discussed in the previous paragraph to include one or more, and in any reasonable combination and/or order, an ultrafiltration step, a filtration step to remove particulates prior to loading onto an anion exchange chromatography column, an alternative or orthogonal chromatography step (including but not limited to a cationic exchange chromatography step, hydroxyapatite chromatography, and/or reversed-phase adsorption chromatography steps (e.g., using Amberlite XAD), and/or a sterile filtration step.

Therefore, the present invention relates to various methods of purifying viral particles, such as adenovirus, which is more economical and robust than known processes. Prior chromatographic applications for adenovirus purification relied on the combination of high nuclease concentrations and low adenovirus loading in order to generate satisfactory results. These factors lead to processes that are uneconomical and impractical upon scale-up. The present invention overcomes these problems by disclosing methods of purifying virus particles, especially adenovirus particles, which comprises an upstream selective precipitation step which removes the vast majority of host cellular DNA when coupled to a clarification step. This early step to remove host cell contaminants allows for the inclusion or exclusion of various downstream steps in various combinations and/or step order, depending upon the level of purity required for the final purified viral product. As examples, but not limitations, additional downstream steps include anion exchange chromatography, ultrafiltration and a downstream low concentration nuclease treatment. More specifically, a preferred additional step subsequent to a selective precipitation step is an anion exchange chromatography step wherein little or no nuclease is added. It is shown herein that this process allows for loading approximately 5-20 times the previously reported amount of adenovirus onto the column due to previous precipitation of contaminants. Such a step will be useful for generating a high purity product. Also, a process incorporating selective DNA precipitation/clarification significantly improves the efficiency of a subsequent ultrafiltration step. And as noted herein, a nuclease treatment step is not required but may optionally be added to ensure process robustness. For many applications, the purity of the ultrafiltered product may be sufficient and chromatographic purification deemed unnecessary. For very high purity applications, such as clinical grade lots or commercial fills, or for alternative reasons such as clearance validation, one of more chromatography steps may be added. As mentioned above, anion exchange chromatography is extremely useful in such a process, depending upon careful resin selection and operating conditions (NaCl concentration), as well as inclusion of a detergent (e.g. PS-80) in the running buffers to inhibit aggregation during loading and elution. Again, overall AEX resin utilization is improved 5-20 fold over the best reported methods, with usable capacity exemplified, but not limited to, $2.0 \times 10^{13}$ vp/mL resin. As an alternative or in addition to anion exchange chromatography, reversed-phase adsorption also may be useful to reduce the concentration of impurities. In particular, detergents introduced during culture, lysis or precipitation may be selectively removed using a batch or column-based adsorption step.

To this end, the present invention relates to a method of purifying virus particles, especially adenovirus particles, which features an early post-lysis selective precipitation step which may be used in further combination with a clarification step and optional steps of ultrafiltration, nuclease treatment, volume reduction and/or buffer exchange.

The present invention also relates to a method of purifying virus particles, especially adenovirus particles, wherein a post-lysis selective DNA precipitation step is utilized in combination with a clarification step, an anion exchange chromatography step and an ultrafiltration step, with optional treatments including but not limited to a nuclease treatment, volume reduction and/or buffer exchange.

The present invention further relates to an exemplified method of purifying virus particles, especially recombinant adenovirus vector particles, as described in Table 1.

The present invention further relates to various modifications which become evident to the skilled artisan upon review of this specification, such modifications utilizing a core element of an early, post-lysis selective DNA precipitation step; a step which when combined with a clarification step, sets up the remainder of the purification process by generating a relatively clean product for further manipulation. It will thus become evident upon review of this specification that none, one or more than one additional purification step may be added at the pleasure of the skilled artisan in order to generate a purified viral product. Such additional steps may be steps disclosed herein (e.g., see Table 1) or which would be known in the art.

Therefore, preferred embodiments of the present invention relate to methods of purifying lots of adenovirus which are of clinical grade quality in commercially viable quantities wherein the process comprises at least a post-lysis step of selective precipitation step via addition of an SPA which removes most host cell DNA when coupled with at least the additional steps of clarification and ultrafiltration. Inclusion of this post-lysis precipitation step significantly improves the efficiency of any subsequent ultrafiltration step(s). Therefore, the methodology disclosed herein meets the need for a virus purification scheme which is amenable to large scale, commercial production requirements. The methods described herein are especially useful in gene vaccine/gene therapy arena to overcome many shortcomings of known viral purification procedures. As noted throughout this specification, the methods disclosed herein results in concentrated adenovirus preparations with negligible amounts of DNA contamination. It is preferred that the adenovirus preparations of the present invention contain adenovirus of at least $1 \times 10^{11}$ vp/ml, and preferably greater than $1 \times 10^{12}$ vp/ml, while having a residual host cell DNA level at least less than 100 picograms/$10^{11}$ vp, or further less than 30 picograms/$10^{11}$ vp, preferably less than 10 picograms/$10^{11}$ vp and most preferably less than 5 picograms/$10^{11}$ vp.

It is an object of the present invention to provide for a method of purifying adenovirus, which at least includes the inclusion of a post-lysis selective precipitation step via addition of an SPA which may be coupled with an additional clarification step(s) and an ultrafiltration step(s). This methodology promotes removal of residual nucleic acids and other cellular debris, resulting in a more robust, commercial grade quantities of highly purified adenovirus particles.

It is a further object of the present invention to provide for a method of purifying adenovirus, which at least includes incorporating the four steps described above, namely (1) cell lysis; (2) selective precipitation of nucleic acid molecules via addition of an SPA; (3) clarification; (4) a concentration step (with or without a nuclease treatment); with the additional step of (5) an anion exchange chromatography step.

It is another object of the present invention to provide for a method of purifying adenovirus, which at least includes incorporating steps in addition to steps 1-5 of the previous paragraph, which may include in any reasonable combination and order, an ultrafiltration step(s), a filtration step to remove particulates prior to loading onto an anion exchange chromatography column, an alternative or orthogonal chromatography step (including but not limited to a cationic exchange chromatography step, hydroxyapatite chromatography, and/or reversed-phase adsorption chromatography and/or a sterile filtration step).

Yet another object of the present invention is exemplified as a method of purifying adenovirus, which includes, but does not necessarily require each of the following process steps: (1) releasing virus particles from infected cells by a lysis step such as a detergent lysis step; (2) selective precipitation to remove a high percentage of contaminating nucleic acids; (3) depth filtration and/or centrifugation to remove cell debris and nucleic acid precipitate; (4) ultrafiltration to reduce volume and exchange buffer; (5) nuclease treatment to digest remaining nucleic acids and facilitate removal; (6) anion exchange chromatography to purify virus away from cellular contaminants and unassembled virus components; (7) tangential flow ultrafiltration to further remove contaminants as well as introducing a formulation buffer; (8) sterile filtration of the virus preparation; (9) optionally including an additional step(s) to further purify the viral preparation, such as a flow-through cationic exchange chromatography step, a reversed-phase adsorption step, and/or a hydroxyapatite chromatography step; and (10) optionally, a step prior to or in conjunction with anion exchange chromatography which is a filtration step to remove particulates prior to loading on to the anion exchange chromatography column. Table 1 outlines an exemplified, step by step Ad purification process, wherein the combination and/or order of each respective process step may be amenable to adjustment by the artisan.

As used herein, "vp" refers to—viral particle—.

As used herein, "AEX" refers to—anion exchange chromatography—.

As used herein, "CEX" refers to—cation exchange chromatography—.

As used herein, "TFF" refers to—tangential flow filtration—

As used herein, "TNBP" refers to—tri-n-butyl phosphate—

As used herein, "CPC" refers to—cetylpyridinium chloride—.

As used herein, "DB" refers to—domiphen bromide—

As used herein, "CTAB" refers to—cetyl trimethylammonium bromide—

As used herein, "BTC" refers to—benzethonium chloride—

As used herein, "TTA" refers to—tetradecyltrimethylammonium chloride—

As used herein, "PS-80" refers to—polysorbate 80—.

As used herein, "SPA" refers to—selective precipitating agent—. A selective precipitation agent is defined herein as any agent, compound or such which, when added to a preparation which containing a population of virus, such as adenovirus, and contaminating nucleic acid molecules, will affect the selective precipitation of at least a substantial amount of contaminating nucleic acid molecules away from the respective virus.

As used herein, the term "adenovirus" or "Ad" or "AdV" refers to any adenovirus, including but not limited to any adenovirus serotype which is a wild type virus, a modified virus (such as an attenuated virus), and/or a recombinant virus, such as any adenovirus serotype which is, for example, a $1^{st}$ or $2^{nd}$ generation recombinant adenovirus vector which may or may not contain one or more heterologous transgenes inserted within the respective recombinant adenovirus vector.

As used herein, the term "host cell" or "host cell line" refers to any mammalian cell line which supports replication of a respective virus, such as a wild type, modified or recombinant adenovirus. It will be recognized that any such host cell line is grown in culture to an art known growth phase, followed by infection with a seed stock of the respective virus, then followed by additional culture under physiologically acceptable conditions, resulting in the production of an additional population of virus, which can be harvested by the methods disclosed herein.

DETAILED DESCRIPTION OF THE INVENTION

Figure 1:
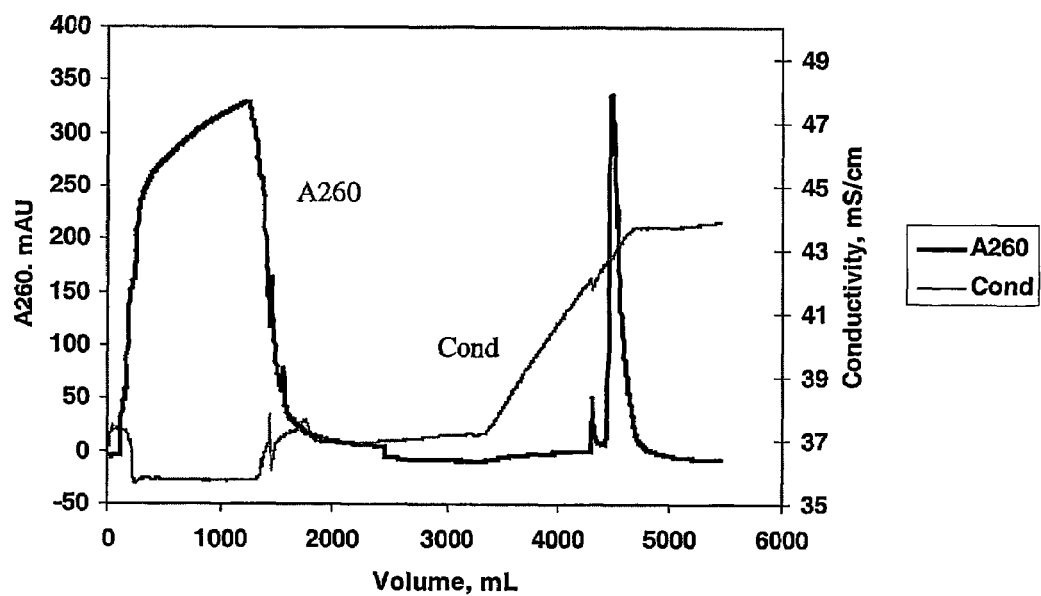
FIG. 1 shows an example of preparative anion exchange (AEX) chromatography. Feed was adjusted to approximately 38 mS/cm and loaded onto Source15Q. The column was washed with 5 volumes of 50 mM HEPES, 2 mM $MgCl_2$, 0.39 M NaCl, 0.1% PS-80, pH 7.5 and a linear gradient was run to 0.47 M NaCl.

The present invention relates to methods of purifying virus particles from a cell lysate. To this end, the present invention relates to methods of purifying virus particles from a cell lysate from a cell culture medium which comprises selectively precipitating impurity (DNA) molecules (such as host cell genomic DNA) away from the virus particles within the cell lysate by adding a selective precipitation agent to the post-lysis host cell culture medium such that at least about 80% of impurity DNA molecules are precipitated away from medium containing the virus particles. As disclosed herein, this initial step allows for the selective precipitation of contaminating DNA, with at least an 80% reduction in contaminating DNA, and as exemplified herein, even about a 90% reduction in DNA following clarification (e.g., depth filtration or centrifugation and a polishing depth filtration step). To this end, the present invention relates to methods of purifying virus, especially adenovirus, where at least 70%, or at least 80%, or even at least 90% of contaminating (e.g., impurity) DNA is removed away from the virus particles after an initial post-lysis step of selective precipitation or an initial post-lysis selective precipitation step followed by a clarification step (e.g., such as depth filtration or centrifugation and a polishing depth filtration step).

While any number of wild type or modified viruses and/or recombinant viral vectors may be amenable to this methodology, a preferred virus is a wild type or modified adenovirus or recombinant adenoviral vector, exemplified herein with a serotype 5, 6 and 35 recombinant adenovirus vector. A preferred virus for purification is any wild type, modified, mutated and/or recombinant adenovirus (again, see Fundamental Biology, $3^{rd}$ Ed., Fields, B. N., Knipe, D. M., and Howley, P. M., Ed., at Chapter 30, pp. 979-1016 (1996)). The present invention relates in part to a purification process whereby a post-lysis step includes at least a selective precipitation step by inclusion of a selective precipitation agent, which is preferably a cationic detergent, which effectively removes the majority of free nucleic acid molecules, as well as other cellular debris. The methodology of the present invention results in recovery of commercially viable quantities of adenovirus vector with excellent purity characteristics, making this methodology especially useful the for filling and distribution of adenoviral-based vaccines or adenoviral-based gene therapy products. The present invention relates to methods of obtaining purified virus from large scale production facilities which includes, in a preferred aspect, a combination of precipitation, depth filtration and/or centrifugation, ultrafiltration, nuclease digestion and chromatography to robustly and economically produce highly purified product. Residual host cell DNA levels are consistently below 5 pg/$10^{11}$ vp when using the methods of the present invention as exemplified in Table 1. It will be evident to the artisan that a measure of the residual host cell DNA content is not meant to be forwarded as a limitation to this methodology. Instead, these data support the essence of the present invention: a large scale methodology for the generation of virus particles which results in a highly purified product which may be utilized in clinical and commercial settings. It can be noted that the importance of achieving particular DNA levels in the final product is product-specific. Products for parenteral use in humans will require the most stringent standards but, even in that case, the goals may vary from 100 pg/dose up to 10 ng/dose ("WHO Requirements for the Use of Animal Cells as in vitro Substrates for the Production of Biologicals (Requirements for Biological Substances No. 50), WHO Technical Report Series, No. 878, 1998) or higher, and are likely to be adjusted depending on the product's indication. In addition, for adenovirus-based products, dosing may vary over several orders-of-magnitude. Therefore, there is no specific significance of achieving a specific residual DNA levels below (such as below 5 pg/$10^{11}$ vp) and, in most applications, variations of several-fold around that level from lot-to-lot are not likely to be consequential. Therefore, as noted above, it is preferred that the adenovirus preparations of the present invention contain adenovirus of at least $1\times10^{11}$ vp/ml, and preferably greater than $1\times10^{12}$ vp/ml, while having a residual host cell DNA level at least less than 100 picograms/$10^{11}$ vp, or further less than 30 picograms/$10^{11}$ vp, preferably less than 10 picograms/$10^{11}$ vp and most preferably less than 5 picograms/$10^{11}$ vp.

The present invention relates in part to a preferred step in the purification process, namely the inclusion of a post-lysis selective precipitation step which, when preferably coupled with clarification, results in removal of residual nucleic acids and other cellular debris, thus allowing preparation of a more robust and economically feasible method for preparing large, commercial grade quantities of highly purified adenovirus particles. The process of the present invention includes, but does not require the following process steps: (1) releasing virus particles from infected cells by a lysis step such as a detergent lysis step; (2) selective precipitation with a SPA to remove a high percentage of contaminating nucleic acids; (3) depth filtration to remove cell debris and nucleic acid precipitate; (4) ultrafiltration to reduce volume and exchange buffer; (5) nuclease treatment to digest remaining nucleic acids and facilitate removal; (6) anion exchange chromatography to purify virus away from cellular contaminants and unassembled virus components; (7) tangential flow ultrafiltration to further remove contaminants as well as introducing a formulation buffer; (8) sterile filtration of the virus preparation; (9) optionally followed by or added as an earlier step an independent, additional step to further purify the viral preparation, such as a flow-through cationic exchange chromatography step, reversed-phased adsorption, and/or a hydroxyapatite step, and (10) optionally, a step prior to or in conjunction with anion exchange chromatography which is a filtration step to remove particulates prior to loading on to the anion exchange chromatography column. Table 1 outlines an exemplified, step by step Ad purification process. As noted herein, an additional option to the process disclosed herein is the addition of a filtration step prior to or in conjunction with anion exchange chromatography. It is possible that in certain cases, (which could depend on the particular components of the culture medium as well as properties of both the production cell line or product), small particulates or "aggregates" may either pass through the primary clarification step or form during nuclease treatment or ultrafiltration, particularly when the ultrafiltration incorporates a concentration step. In this case, an additional filtration step to remove these particulates prior to loading on to the anion exchange chromatography is contemplated. The filter could be placed in line during the loading of the column, or could be used in an independent operation. The filtration would generally be accomplished using disposable capsule or cartridge filters. These dead-end filters could be either depth or membrane-based. The media in these filters could be polypropylene, cellulose, cellulose esters, modified polyvinylidene fluoride, nylon, polyethersulfone, or any other material which is consistent with low product binding; in addition, all of these media could be present with or without modifying agents such as diatomaceous earth and/or resins to improve filter properties. The nominal size of such a filter would be between 0.2 and 1 micron.

The present invention further relates to a process for purifying wild type or recombinant virus, especially wild type or recombinant adenovirus, wherein one or more steps of an exemplified procedure (see Table 1) are omitted. Such an omission may be utilized by the artisan on a mix and match basis in order to generate a complete protocol for purification of adenovirus which is qualitatively acceptable and is formulated at a concentration amenable to clinical and/or commercial applications. Any such modified procedure will preferably, but not necessarily, include at least the following steps: (1) cell lysis; (2) a post-lysis selective DNA precipitation; (3) clarification of the remaining virus-containing supernatant, such as by depth filtration to remove cell debris and additional nucleic acid precipitate; and, (4) an ultrafiltration step, to concentrate the purified virus to levels useful for clinical and/or commercial administrations and/or exchange the virus into an appropriate buffer.

Another embodiment of the present invention relates to the incorporating the four steps described above, namely (1) cell lysis; (2) selective DNA precipitation; (3) clarification; (4) a concentration step (with or without a nuclease treatment); with the additional step of (5), which is an anion exchange chromatography step.

The present invention further relates to incorporation of additional downstream methodology beyond steps 1-5 discussed in the previous paragraph to include one or more, and in any reasonable combination, an ultrafiltration step, an alternative or orthogonal chromatography step (including but not limited to a cationic exchange chromatography step, hydroxyapatite chromatography and/or reversed-phase adsorption chromatography steps (e.g., using Amberlite XAD, and/or a sterile filtration step).

Steps 1-4 can be extended to any product with characteristics allowing for selective precipitation of DNA based on charge and/or hydrophobicity, provided that the product is not inactivated by the selective agent. For example, any cationic product (or anion with lower charge density than DNA) should remain free in solution when precipitating DNA with cationic detergents or polymers. Exemplary products can include but are not limited to adeno-associated virus (AAV), human papilloma virus (HPV) or VLPs derived from it's structural protein(s), and hepatitis A virus (HAV). Of particular interest is AAV, since purification using cation exchange chromatography has been demonstrated and large-scale production facilities may be necessary if approved as a vector for either gene therapy or vaccine products. In that case, cationic detergents could be used to precipitate both host cell DNA and the contaminating helper adenovirus. Following clarification, the AAV could be further processed by ultrafiltration and chromatography, with cation exchange being the preferred step and anion exchange chromatography added only if additional robustness was desired. To this end it should be noted that one aspect of the present invention is the specific use of domiphen bromide as a selective precipitation agent for purification schemes which require the removal of any number of cellular components, especially nucleic acids, away from any number of different types of biological products, including but not limited to virus particles, virus-like particles (e.g., HPV-based vaccine), or any other biological product which may be substantially separated from a contaminating culture-based component via a selective precipitation step. Though a large number of potential SPAs can be used to practice the present invention, domiphen bromide is of particular interest due primarily to its availability as a GMP grade raw material and current use in other products intended for human use. More specifically, since domiphen bromide is extensively used as an active ingredient in oral hygiene products as well as topical antibiotic cremes, this molecule is produced in large quantities and released under cGMP conditions. Use as a selective precipitation agent, and more specifically to the precipitation of nucleic acids away from virus, is not known in the art. The increased selectivity of DB results from its ability to readily discriminate between stream components that possess small differences in charge densities or overall charge. Successful implementation of this technology into streams that have minimal differences in charge density (e.g. adenovirus and DNA) highlights its potential application across a number of current or future commercial applications. The large processing window that accompanies such an application can only increase as larger charge differentials between product and impurities are explored. Selectivity can be further enhanced by the addition of inorganic salts of varying ionic strength. During precipitation, for compounds also incorporating an ammonium group, it is known that positive charges on the detergent molecules neutralize the negatively charged groups on the molecules that possess a degree of electronegativity. Once charges on the molecules are neutralized, the hydrophobic tails of the detergent molecules interact with each other via hydrophobic interactions, making the soluble components precipitate. The DB molecule possesses structural similarity to many commonly used cationic detergents in that it contains a charged ammonium group yet the combination of ammonium group(s), ester(s), and benzene ring(s) provide additional selectivity and robustness to charge based interactions that such a novel technology may be implemented (e.g. including but not limited to DNA, RNA, Proteins, VLPs, and polysaccharide molecules).

The present invention thus relates to methodology which results in the purification of adenovirus vector particles from large scale production facilities which render commercially viable amounts of recovered virus as well as also showing excellent purity characteristics. The term "large scale" as used herein is considered to be total host cell culture volumes of greater than about 10 liters up to about 50,000 liters, with runs from about 300 liters to about 20,000 liters being the norm.

In one exemplified aspect of the present invention, a combination of cell lysis, precipitation with an SPA, depth filtration and/or centrifugation, ultrafiltration, nuclease digestion and chromatography steps are utilized to robustly and economically produce highly purified product, resulting in residual host cell DNA levels at less than detectable levels when using a Q-PCR assay for host cell DNA. An initial lysis step provides maximum release of intracellular adenovirus from the host cells and provides for a potential to inactivate potential adventitious agents (in particular, enveloped viruses such as herpesviruses or retroviruses) which could hypothetically contaminate the cell culture at a low level.

As noted above, a first step lysis of infected cells allows for harvest of both cell-associated (intracellular) and non-associated (extracellular) virus from the host cell culture medium. As a result, it provides flexibility in selection of culture conditions which are optimal for overall virus productivity. In addition, the presence of detergent throughout the process minimizes association of the virus with host cell DNA. Host cell detergent lysis, while being the preferred method of lysing AdV-containing host cells, can be replaced by non-mechanical lysis methods amenable to large scale purification methods (such as enzyme treatment) and/or mechanical shear methods (such as hollow fiber ultrafiltration) to release maximum amounts of adenovirus. Any cell lysing component amenable to introduction into a biological system such as a gene therapy or vaccine purification protocol may be used to lyse the infected host cells, namely a detergent or enzyme known in the art to be useful in biological applications is contemplated, including but not limited to detergents Triton and/or Polysorbate-80. In addition, a solvent such as TNBP can be added to the lysate or clarified lysate at low concentrations (e.g. 0.3%) to complement these detergents in their ability to inactivate enveloped viruses. Also, autolysis of the infected host cells may provide for substantial release of intracellular virus. Therefore, any form of host cell lysis which is known in the art may be used to liberate intracellular virus into the host cell culture medium for eventual harvesting by the methods disclosed herein.

Following lysis, DNA is selectively precipitated by addition of a concentrated SPA solution while leaving the adenovirus in the liquid phase. This step allows for the selective precipitation of host cell DNA and also improves downstream robustness. As exemplified herein, this early stage precipitation step results in about a 90% reduction in nucleic acid following clarification. Nucleases (including but in no way limited to BENZONASE™ (EM Industries), DNases, and RNases) are no longer required but may still be beneficial for maximum DNA reduction. In view of the ability of this precipitation step to remove the vast majority of the contaminating nucleic acids, anion exchange chromatography may not be essential for product purity depending on the final dosage. However, an AEX step may remain in the process for robustness.

While not being bound by theory, it is believed that the addition of an SPA following cell lysis results in the positively charged groups (and aromatic rings, if present) on the compounds binding to the negatively charged phosphate groups (and base pairs) on the DNA molecules. The hydrophobic tails on the detergents then interact with each other resulting in precipitation. Experimental results disclosed herein show that DNA molecules have higher affinity to the SPAs than adenovirus, therefore the molecules will not interact with the adenovirus until the DNA concentration in the liquid phase is low. Mixed micelles also provide increased robustness. This mechanism provides the required selectivity during precipitation. The SPAs which may be useful in practicing the invention described herein include, but are in no way limited to, amine copolymers, quaternary ammonium compounds, and any respective mixtures thereof. Mixtures of SPAs provide similar performance to pure SPAs while incorporating multiple precipitation mechanisms (i.e. primary binding sites). A mixture of SPAs may be added to the cell lysate as the precipitation buffer or a high-cut/low-cut methodology of addition may be incorporated. More specifically, the many forms of polyethylene imine (PEI) have shown they are very effective in neutralization of excess anionic charge (DNA impurities), especially under acidic and neutral pH conditions. Theoretically, modified PEI copolymers having relatively high molecular mass can be as efficient.

Quaternary ammonium compounds of the following seven classes have been the most beneficial for the present invention. These include but are not limited to the following classes and examples of commercially available products: Monoalkyltrimethyl ammonium salts (Examples of commercially available products include cetyltrimethylammonium bromide or chloride as CTAB, tetradecyltrimethylammonium bromide or chloride (TTA), alkyltrimethyl ammonium chloride, alkylaryltrimethyl ammonium chloride, dodecyltrimethylammonium bromide or chloride, dodecyldimethyl-2-phenoxyethylammonium bromide, hexadecylamine: chloride or bromide salt, dodecyl amine or chloride salt, and cetyldimethylethyl ammonium bromide or chloride.), Monoalkyldimethylbenzyl ammonium salts (Examples include alkyldimethylbenzyl ammonium chlorides and benzethonium chloride as BTC), Dialkyldimethyl ammonium salts (Commercial products include domiphen bromide as DB, didecyldimethyl ammonium halides, and octyldodecyldimethyl ammonium chloride or bromide.), Heteroaromatic ammonium salts (Commercial products include cetylpyridium halides (CPC or bromide salt and hexadecylpyridinium bromide or chloride), cis-isomer 1-[3-chloroallyl]-3,5,7-triaza-1-azoniaadamantane, alkyl-isoquinolinium bromide, and alkyldimethylnaphthylmethyl ammonium chloride (BTC 1110). Polysubstituted quaternary ammonium salts, (Commercially available products include, but are not limited to alkyldimethylbenzyl ammonium saccharinate and alkyldimethylethylbenzyl ammonium cyclohexylsulfamate), Bis-quaternary ammonium salts (Product examples include 1,10-bis(2-methyl-4-aminoquinolinium chloride)-decane, 1,6-Bis{1-methyl-3-(2,2,6-trimethyl cyclohexyl)-propyldimethyl ammonium chloride] hexane or triclobisonium chloride, and the bis-quat referred to as CDQ by Buckman Brochures.), and Polymeric quaternary ammonium salts (Includes polyionenes such as poly [oxyethylene(dimethyliminio)ethylene(dimethyliminio)ethylene dichloride], poly[N-3-dimethylammonio)propyl]N-[3-ethylneoxyethylenedimethylammonio) propyl]urea dichloride, and alpha-4-[1-tris(2-hydroxyethyle)ammonium chloride).

The SPA-treated cell lysate is clarified by depth filtration to remove precipitated impurities and cell debris. Centrifugation with or without polishing depth filtration also is feasible. Therefore, clarification of precipitated lysate may be accomplished using centrifugation alone, or centrifugation in tandem with a polishing clarification step such as depth filtration. For larger volumes of liquid (greater than approximately 50 L), continuous centrifugation will be preferred over batch methods. The continuous centrifuge may be a tubular design, as in the CARR Powerfuge, or disk, as in the Westfalia CSA-1, though other manufacturers and models are likely to be satisfactory. In general, residence times and required centrifugal force will be dictated by the efficiency of the individual equipment as well as the precipitate size distribution, and the methodology for selecting conditions appropriate to remove precipitate but not adenovirus will be apparent to any skilled in the art. Example 15 shows the use of continuous centrifugation followed by a polishing depth filtration. The use of continuous centrifugation is preferred in applications where the cell density is high (e.g. fed-batch or perfusion culture) and/or when volumes are very large (greater than 1000 L). The clarified cell lysate is then concentrated as appropriate (depending on the cell mass and adenovirus productivity of culture, with 10-20 fold being typical of simple batch processes), optionally nuclease-treated, and diafiltered. The combination of the precipitation and clarification remove approximately 90% of total DNA and, depending on the ultrafiltration/nuclease-treatment conditions, the purity of this stream may be sufficient for many applications. The process does not require nuclease, though small amounts may be used to ensure process robustness. For many applications, the purity of the ultrafiltered product may be sufficient and chromatographic purification deemed unnecessary. For very high purity applications (or for alternative reasons such as clearance validation), one of more chromatography steps may be added, as discussed herein. It will be within the purview of the artisan to test potential substitutes for the SPAs disclosed herein to identify a compound which effectively precipitates nucleic acid molecules and other cellular debris away from virus particles as exemplified herein for domiphen bromide (DB). Therefore, this present invention relates in part to methods of purifying virus particles from a host cell culture medium which comprises selectively precipitating host cell nucleic acid molecules away from the virus particles within the post-lysis host cell culture medium by adding a selective precipitation agent to the post-lysis host cell culture medium. Under such conditions it will be expected that a substantial majority of contaminating nucleic acids will be precipitated away from the virus, from at least 70%, more likely at least 80% of such contaminating DNA and up to at least 90% of such contaminating/imurity DNA, especially when followed by a clarification step such as depth filtration alone or depth filtration combined with a polishing depth filtration step.

It is exemplified herein and preferred that the selective precipitation step occur as the first step after cell lysis. However, this preference is by no means a limitation, as the selective precipitation step may be inserted at other stages of the purification process to better remove residual nucleic acid molecules and cellular debris from a buffered cell lysate or later stage Ad-containing buffer solution. For example, detergent precipitation can alternatively be placed after clarification or ultrafiltration (concentration/diafiltration) with the addition of a subsequent clarification. The additional clarification may take any of several forms including depth or membrane filtration.

A filtration step may be contemplated to remove cell debris and nucleic acid precipitate. This step provides a convenient means to economically remove cell debris and precipitate. In choosing a filter or filter scheme it was necessary to ensure a robust performance in the event upstream changes or variations occur. Maintaining the balance between good clarification performance and step yield requires investigation of a large variety of filter types with varying internal media. Suitable filters may utilize cellulose filters, regenerated cellulose fibers, cellulose fibers combined with inorganic filter aids (e.g. diatomaceous earth, perlite, fumed silica), cellulose fibers combined with inorganic filter aids and organic resins, or any combination thereof, and polymeric filters (examples include but are not limited to nylon, polypropylene, polyethersulfone) to achieve effective removal and acceptable virus recoveries. In general, a multiple stage process is preferable but not required. An exemplary two or three-stage process would consist of a coarse filter(s) to remove large precipitate and cell debris followed by polishing second stage filter(s) to with nominal pore sizes greater than 0.2 micron but less than 1 micron. The optimal combination will be a function of the precipitate size distribution as well as other variables. In addition, single stage operations employing a relatively tight filter or centrifugation may also produce a product of good quality. More generally, any clarification approach including dead-end filtration, microfiltration, centrifugation, or body feed of filter aids (e.g. diatomaceous earth) in combination with dead-end or depth filtration, which provides a filtrate of suitable clarity to not foul the membrane and/or resin in the subsequent steps, will be acceptable to practice within the present invention.

Depth filtration or depth filtrations in combination with centrifugation have been the most robust methods of clarification for the present invention. These include but are not limited to the following examples of commercially available products: CUNO Incorporated AP series depth filters (Examples include AP01), CUNO Incorporated CP series depth filters (Example include CP10, CP30, CP50, CP60, CP70, CP90), CUNO Incorporated HP series depth filters (Examples include HP10, HP30, HP50, HP60, HP70, HP90), CUNO Incorporated CA series depth filters (Examples include CA10, CA30, CA50, CA60, CA70, CA90), CUNO Incorporated SP series depth filters (Examples include SP10, SP30, SP50, SP60, SP70, SP90), CUNO Delipid and Delipid Plus filters, Millipore Corporation CE series depth filters (Examples include CE15, CE20, CE25, CE30, CE35, CE40, CE45, CE50, CE70, CE75), Millipore Corporation DE series depth filters (Examples include DE25, DE30, DE35, DE40, DE45, DE50, DE55, DE560, DE65, DE70, DE75), Millipore Corporation HC filters (Examples include A1HC, B1HC, COHC), CUNO Polynet Filters (An example include Polynet-PB), Millipore Clarigard and Polygard filters, CUNO Life Assure filters, ManCel Associates depth filters (Examples include but are not limited to PR 12 UP, PR12, PR 5 UP), and PALL or SeitzSchenk Incorporated filters (Examples include but are not limited to Bio20, SUPRA EKIP, KS-50P).

An additional aspect of the disclosed process are a series of steps to concentrate the Adenovirus, add an additional nuclease treatment (e.g. BENZONASE™, EM Industries) and to introduce an exchange buffer via diafiltration. The selected membrane size allows for clearance of unassembled virus structural proteins, detergent and nuclease. The addition of BENZONASE™ is not required to derive a product which is highly pure by anion exchange HPLC but does lead to lower residual DNA levels at the end of this step and presumably in the final purified product.

The particular ultrafiltration membrane selected will be of a size sufficiently small to retain adenovirus but large enough to effectively clear impurities. Depending on the manufacturer and membrane type, nominal molecular weight cutoffs (NMWCO) between 100 and 1000 kDa may be appropriate. The membrane composition may be, but is not limited to, regenerated cellulose, polyethersulfone, polysulfone, or derivatives thereof. These membranes can be flat sheets or hollow fibers. Ultrafiltration using tangential flow mode is preferred. Turbulence-promoting screens may also be useful to optimize impurity clearance. In a preferred embodiment, 300 kDa or 500 kDa NMWCO PES flat sheet membranes with a turbulence-promoting screen (e.g. Millipore Pellicon 2 Biomax with C screen) are used in tangential flow mode. In tangential flow mode, the step may be controlled by setting a fixed cross-flow with or without backpressure on the retentate return, setting a fixed transmembrane pressure, or fixing both the cross-flow and the permeate flux.

The concentration factor targeted during ultrafiltration will be a function of culture conditions, including the medium used, cell density, and viral productivity. For batch culture with infection cell density of approximately $10^6$ cells/mL, 5- to 40-fold concentration is preferred; 10- and 25-fold concentration is especially preferred.

Nuclease treatment can also be considered for inclusion in the process, but is by no means required. Nuclease treatment can include the use of a broad spectrum nuclease (e.g. BENZONASE™), a DNase, a RNase, or any combination thereof. A nuclease or cocktail with both RNase and DNase activity is preferred. A nuclease treatment step can be contemplated at any point in the process, as long as residual nuclease content in the final product is acceptable to the application. It is preferred that nuclease treatment occur after clarification, and especially preferred that nuclease treatment occur after clarification and a concentration step, but before an anion exchange chromatography step. One useful manifestation of the process allows for nuclease treatment in the ultrafiltration apparatus after concentration. Permeation can be temporarily halted for an appropriate length incubation, and then restarted for diafiltration.

Diafiltration into a buffer using ultrafiltration may be desirable. In most applications, several batch volumes of buffer will be used to ensure for complete exchange. If the process is to end at this point, an appropriate formulation buffer (e.g., see PCT publication WO 01/66137) can be used to maximize product stability. If the stream is to loaded onto a chromatography column, the diafiltration should be conducted into a buffer appropriate for that application. For example, if the product is to be loaded on to an anion exchange column, diafiltration into a buffer with pH between 6.5 and 8.0 is preferred, though not required. More specifically, diafiltration into 50 mM HEPES, 2 mM $MgCl_2$, 1 M NaCl, pH 7.5, with or without detergent to prevent aggregation (such as 0.1% PS-80), may be appropriate.

TABLE 1

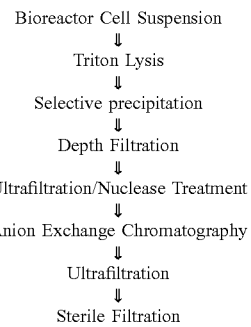

As noted throughout this specification and as shown in Table 1, an anion exchange chromatography step also may be useful for many applications. For adenovirus type 5 purification with Source15Q, the NaCl concentration for loading and washing could presumably be anywhere from 0.33 to 0.41 M at pH 7.5 and would shift at alternative pH's. The pH of the buffers needs to be high enough for adenovirus to bind (greater than approximately 6.5). In addition, the pH of the buffer system should also be low enough to avoid viral instability. The precise maximum pH which is usable will depend on the specific stability profile of the adenovirus serotype and the buffer components, and can easily be determined by the artisan for that particular application. As a guide and certainly not a limitation, a pH range from Ad5 could potentially range from about 6-10, with preferred levels of 6.5-9, and even more preferred of 6.5-8.0. The presence of 0.1% PS-80 in the buffers is critical to achieving low residual DNA levels in the product because it attenuates virus/DNA association and virus aggregation. It will be within the realm of routine experimentation for the artisan of ordinary skill to establish higher or lower detergent concentrations or alternative detergents which would be useful to promote dissociation of virus particles away from other virus as well as various cell contaminants. It is also within this same realm of experimentation that the artisan may choose an alternative detergent to the process buffer. As an example, but in no way meant as a limitation, non-ionic surfactants which could potentially be used to inhibit aggregation in anion exchange and throughout the process include polyoxyethylene sorbitan fatty acid esters, including but not limited to Polysorbate-80 (Tween 80®) [as exemplified herein], Polysorbate-60 (Tween 60®), Polysorbate-40 (Tween 40®), and Polysorbate-20 (Tween 20®), polyoxyethylene alkyl ethers, including but not limited to Brij 58®, Brij 35®, as well as others such as Triton X-100®, Triton X-114®, NP40®, Span 85 and the Pluronic series of nonionic surfactants (e.g. Pluronic 121). Of these, the Polysorbate series are preferred. It is disclosed herein that a resin such as a Source 15Q resin (Amersham Biosciences) has a extremely high binding capacity for adenovirus which can be effectively utilized due to inhibition of aggregation. Anecdotal evidence and known art suggest that low loadings ($<1\times10^{12}$ vp/mL resin) are the industry norm. For Source 15Q, columns with bed heights in excess of 5 cm are preferred when the column diameter exceeds 10 cm. Columns with bed heights between 10 and 25 cm work especially well. Although not required, it is preferably to implement a strategy which fractionates the main product peak from chromatographically-related impurities, for example, by employing a cutoff value for UV absorbance. Other resins which are suitable for adenovirus purification in this process include but are in no way limited to Source 30Q (Amersham Biosciences), Fractogel TMAE (EM Industries), and Q-Sepharose XL (Amersham Biosciences). Any anion exchanger should be usable, others we have demonstrated include Fractogel DEAE (EM Industries), Q-Hyper D/F (Biosepra), Toyopearl DEAE-650M (Tosohaas), Toyopearl DEAE-750C (Tosohaas), and Toyopearl QAE-550C (Tosohaas). In addition, anion exchange membrane chromatography products such as those produced by Pall (e.g Mustang™ series) and Sartorius (e.g. Sartobind series) are suitable for adenovirus purification.

In any particular embodiment of the present invention, the anion exchange product can be diafiltered into formulation buffer and sterile filtered. Alternatively, an additional chromatography step (e.g. cation exchange) may be added either before or after the diafiltration with the potential to improve the robustness of impurity and/or virus/prion clearance. Tangential flow ultrafiltration is useful in removing residual protein and nucleic acid and to exchange the virus into a formulation buffer. This step provides PS-80 control and can provide clearance of residual impurities including DNA, residual detergents and host cell proteins. The presence of PS-80 in the feed and diafiltration buffer minimizes the potential for product aggregation. Flux control is important for the effective reduction of PS-80 in the presence of high adenovirus concentrations. The choice between 300 kD and 500 kD membranes is dictated by the tradeoffs between yield and improved impurity clearance. Other membrane configurations (such as a hollow fiber) are acceptable substitutes. More generally, the selection of conditions for this ultrafiltration is similar to those described earlier. That is, the particular ultrafiltration membrane selected will be of a size sufficiently small to retain adenovirus but large enough to effectively clear impurities. Depending on the manufacturer and membrane type, nominal molecular weight cutoffs (NMWCO) between 100 and 1000 kDa may be appropriate. The membrane composition may be, but is not limited to, regenerated cellulose, polyethersulfone, polysulfone, or derivatives thereof. These membranes can be flat sheets or hollow fibers. Ultrafiltration using tangential flow mode is preferred. Turbulence-promoting screens may also be useful to optimize impurity clearance. In one embodiment, 300 kDa or 500 kDa NMWCO PES flat sheet membranes with a turbulence-promoting screen (e.g. Millipore Pellicon 2 Biomax with C screen) are used in tangential flow mode. In tangential flow mode, the step may be controlled by setting a fixed cross-flow (with or without backpressure on retentate return line), setting a fixed transmembrane pressure, or fixing both the cross-flow and the permeate flux. Controlling the cross-flow and permeate flux is preferred. The particular diafiltration buffer chosen should be an appropriate formulation buffer (see WO 0166137) or a subset of the desired components. Examples include, but are not limited to (1) 5 mM Tris, 1 mM $MgCl_2$, 75 mM NaCl, 5% sucrose, 0.005% PS-80, pH 8.0, (2) 10 mM Tris, 10 mM Histidine, 1 mM $MgCl_2$, 75 mM NaCl, 5% sucrose, 0.005% PS-80, pH 7.4, (3) 5 mM Tris, 10 mM NaCl, 1 mM $MgCl_2$, 5% sucrose, 0.005% PS-80, pH 7.4, and (4) 10 mM Tris, 10 mM Histidine, 1 mM $MgCl_2$, 75 mM NaCl, 5% sucrose, 0.02% PS-80, 0.1 mM EDTA, 0.5% (v/v) ethanol, pH 7.4.

A sterile filtration step may be included, which is helpful in eliminating bioburden. The product can be filtered through a 0.22 micron modified polyvinylidene fluoride (PVDF) membrane (e.g. Millipore Millipak). In addition to modified PVDF, the sterile filter may be constructed of a variety of other materials that are well known in the art and available to the artisan. These may include but are not limited to polypropylene, cellulose, cellulose esters, nylon, polyethersulfone, or any other material which is consistent with low product binding. The filter may have a single membrane layer or may incorporate a prefilter of the same or different material. The product can be held frozen or at approximately 4 C for subsequent formulation and filling. An additional optional step downstream in the process is the inclusion of an orthogonal purification step in order to clear any remaining impurities and/or other agents. One such step includes, but is not necessarily limited to, a cation exchange chromatography step. If chosen, operation of the cation exchange step should be in flow through mode. The second ultrafiltration is operated as before except the salt concentration of the diafiltration buffer may be reduced (for example, to 10 mM). After ultrafiltration and immediately before cation exchange, the pH of the batch is reduced to 6.5 via addition of a low pH buffer (Histidine). Lower pHs may be achievable but risk adenovirus loss in the exemplified formulation buffer; higher pHs reduce efficacy of the step but improve adenovirus stability. Similarly, the NaCl concentration can be varied. To date, a number of resins have been evaluated for adenovirus recovery including Poros 50HS, Source 30S, Source 15S, SP Sepharose HP, SP Sepharose XL, SP Sepharose FF; Source 30S is preferred. Immediately following cation exchange, the pH is increased to the formulation target through the addition of a high pH Tris buffer. In addition and as noted above, anion exchange membrane chromatography products such as those produced by Pall (e.g Mustang™ series) and Sartorius (e.g. Sartobind series) are suitable for adenovirus purification. The product can then be sterile filtered as before.

A reversed-phase adsorption step also may be added, preferably following clarification or the first ultrafiltration step. Reversed-phase adsorption can remove detergents including Triton X-100 and domiphen bromide as well as culture media components such as Pluronic and phenol red as well as a variety of other hydrophobic impurities. Therefore it represents a convenient method to increase process robustness or eliminate downstream steps. The adsorption step may be operated in either batch or column mode. In batch mode, the adsorbent would subsequently be removed using a filtration, preferably in dead-end mode. In column mode, the batch would be pumped over the resin at a suitable residence time to allow for adsorption of detergents and other impurities. Suitable resins should have a pore size which excludes the product and can include any of the Amberlite XAD series, e.g. XAD4, XAD16, XAD1600, XAD1180 (Rohm and Haas) or similar resins from other manufacturers e.g. Bio-Beads SM2 (Bio-Rad).

A hydroxyapatite chromatography step also can be considered for removing additional impurities. This step can be operated in either bind/elute or flow-through modes. The step can be placed after either ultrafiltration step by ending the UF with a diafiltration into a buffer with approximately 10 mM phosphate and 0.5 M NaCl at a preferred pH between 6.5 and 8. A gradient in phosphate to 0.4 M is sufficient for adenovirus elution.

It will become evident upon review of this specification that the processes of the present invention are scaleable, running the gamut from smaller scale cell cultures (e.g., about 5-10 liter runs) all the way to commercial scale preparations, such as 10,000 to 50,000 L production runs. Example sections 2 and 5 show data from complete smaller scale runs, while the discussion below in this section contemplates, as an example and certainly not a limitation, an adenovirus purification procedure from an 1000 liter (L) culture (800 L working volume) of PER.C6™ cells (Crucell) previously infected with the respective adenovirus vector. To this end, Table 1 summarizes the process descriptors for a prophetic 1000 L bioreactor run (800 L working volume) but will be linearly scalable. The initial process steps (lysis, depth filtration, and ultrafiltration) scale with culture volume while the anion exchange chromatography and subsequent steps scale with viral particle input. Therefore, the size of the latter steps will be based on a bioreactor productivity estimate of $4 \times 10^{13}$ virus particles per liter (vp/L). Under these assumptions, approximately $1.6 \times 10^{16}$ vp will be produced per lot. Additionally, Example 9 shows data generated from a 600 L Ad5 run.

A first step in a purification process of the present invention is a host cell lysis step, which provides for maximum release of adenovirus particles from the cells as well as providing for an opportunity to potentially inactivate adventitious agents. As mentioned earlier, a solvent (e.g. TNBP) also can be added at low concentration (i.e., 0.3%) to increase the efficiency of inactivation of adventitious agents. The prolonged hold of a lysate or clarified lysate stream incorporating TNBP may potentially lead to a decrease in product infectivity. From an 800 L adenovirus culture process, approximately 8 liters of 10% Triton X-100 and 40 liters of 0.5 M Tris, 40 mM $MgCl_2$, 1% PS-80 will be added to the bioreactor with mild agitation. Cell lysis will be complete within 2 hours but may be held for additional time for viral clearance purposes. The cell lysate may then be held at 4° C. or immediately purified. This initial lysis step, regardless of the scale of the adenovirus culture, allows for harvest of both cell-associated (intracellular) and non-associated virus (extracellular). As a result, it will provide flexibility in selection of culture conditions which are optimal for overall virus productivity. In addition, the presence of detergent throughout the process will minimizes association of the virus with host cell DNA.

As noted above, a preferred purification scheme incorporates a step to precipitate host cell nucleic acid molecules and other cellular debris as well as improve downstream robustness. Continuing a description of a projected purification procedure for a 800 L run, approximately 60 L of 0.5% domiphen bromide (CTAB or CPC may be substituted with some adjustment of the final concentration), is slowly added to the bioreactor or harvest tank for a final concentration of approximately 0.04%. If necessary, the optimum SPA concentration for a specific run may be determined using probe studies at 1 mL scale. The sub-surface addition of the SPA is preferred but not required. The precipitated lysate is immediately clarified. Such a precipitation will result in approximately a 90% reduction in nucleic acid following clarification. In addition, other impurities (cell debris, etc.) may also be flocculated during this precipitation. When compared with unprecipitated controls, the throughput of depth filtration may be dramatically enhanced and yields across depth filtration may be improved. The clarified product from such an 800 L run will be significantly less turbid and the subsequent ultrafiltration performance will also be markedly improved. Nucleases (e.g. BENZONASE™ and RNases) will no longer be required but may still be beneficial for maximum DNA reduction. Anion exchange chromatography may not be essential for product purity depending on the final dosage but, as shown in this prophetic example as well as Example Sections 2 and 5 may remain in the process for robustness.

The SPA-treated cell lysate is clarified to remove precipitated impurities and cell debris. This step may include either a depth filtration step or a centrifugation step with or without a depth filtration polishing step. Whichever step is incorporated, the clarified cell lysate will then be concentrated 10-20 fold, optionally treated with nuclease, and diafiltered. The combination of the precipitation and clarification will remove approximately 90% of total DNA and, depending on the ultrafiltration/nuclease-treatment conditions, the purity of this stream may be sufficient for many applications. More specifically, a depth filtration step will be useful to remove cell debris and host nucleic acids. When opting for depth filtration, the cell lysate will be filtered through two depth filters in series to remove cell debris. The filtration will utilize two 16 inch Millipore Millistak CE20 filter cartridges (75 $ft^2$) followed by two 16 inch Millistak CE50 cartridges (75 $ft^2$). These areas include a safety factor of at least 2. The filtration will be conducted using a constant flow rate of approximately 9 L/h/$ft^2$. Liquid remaining in the housing will be displaced with air pressure. Depth filtration provides a convenient means to economically remove cell debris and precipitate. It will be known to the skilled artisan at least upon review of this specification that the actual filter selection may be changed to further optimize yield or impurity clearance. As noted previously, centrifugation is a viable alternative to depth filtration that may be especially applicable at larger scale runs.

In the purification scheme as shown in Table 1, concentration, nuclease treatment, and diafiltration steps are incorporated in order to reduce batch volume, digest and remove residual nucleic acids, and to promote a buffer exchange. More specifically, the clarified lysate will be concentrated from approximately 800 L to approximately 40 L using a constant-volume ultrafiltration with a 300 kD NMWCO polyethersulfone (PES) membrane under constant flux conditions. Following concentration, 0.6 MM Units of BENZONASE™ (15 U/mL) will be added directly to the retentate and slowly recirculated in the ultrafiltration system with mixing. After 1-2 hours at room temperature, the batch will be diafiltered against 5 volumes (200 L) of 50 mM HEPES, 2 mM $MgCl_2$, 1 M NaCl, pH 7.5 under constant flux conditions. It should be noted that the selected membrane size will allow for clearance of unassembled virus structural proteins, detergent micelles and BENZONASE™. A larger MWCO (eg 500 kD) may also provide suitable performance. The addition of BENZONASE™ is not required to derive a peak which is highly pure by anion exchange HPLC but will lead to lower residual DNA levels at the end of this step and presumably in the final purified product.

The anion exchange chromatography (AEX) step of Table 1 will be useful to purify the virus from host cell proteins, nucleic acids, and unassembled viral components. The conductivity of the batch will be adjusted to 38 mS by the addition of approximately 62 L of 50 mM HEPES, 2 mM $MgCl_2$, 0.1% PS-80, pH 7.5. Following dilution, the batch will be pumped on to a column of Source 15Q resin (Amersham Biosciences) at a loading of approximately $5×10^{12}$ particles per mL resin. For MRKAd5gag, this corresponds to a ca. 5 liter column (ca. 20 cm H×16 cm D). Following loading, the column will be washed with 5 volumes of 50 mM HEPES, 2 mM $MgCl_2$, 0.39 M NaCl, 0.1% PS-80, pH 7.5 to remove residual Triton and protein impurities. Product is then eluted in a 4 volume linear gradient to 0.47 M NaCl and is collected based on the $A_{260}$ signal. The need to control temperature during this process will be dictated by processing time and the stability of the AdV at this stage. Loading at a conductivity of 38 mS is approximately equivalent to 0.38 M NaCl. The salt concentration is suitable to bind adenovirus particles but not related impurities; this translates into a higher binding capacity for adenovirus. The presence of 0.1% PS-80 (or a related compound in a biologically effective concentration) in the buffers will be critical to achieving low residual DNA levels in the product because it attenuates virus/DNA association and virus aggregation. The Source 15Q resin has a extremely high binding capacity for adenovirus which can be effectively utilized because we are inhibiting aggregation.

Tangential flow ultrafiltration is a step shown in Table 1 which is useful to also remove residual protein and nucleic acid as well as for exchanging virus into a formulation buffer. Briefly, the area of membrane (300 kD MWCO PES) is selected for a loading of $1-2×10^{16}$ vp per $m^2$. The AEX product will be diluted to ca. $1.1×10^{12}$ vp/mL (approximately 16 liters) and is then diafiltered using flux control against 5 volumes of formulation buffer (5 mM Tris, 1 mM $MgCl_2$, 75 mM NaCl, 5% sucrose, 0.005% PS-80, pH 8.0). The step is operated at approximately 4° C. and the product is held at 4° C. until sterile filtration. This step will provide PS-80 control and can provide clearance of residual impurities including DNA and host cell proteins. The presence of PS-80 in the feed and diafiltration buffer will minimize the potential for product aggregation. Flux control is important for the effective reduction of PS-80 in the presence of high adenovirus concentrations. 500 kD membranes may be substituted, however, there is some potential for virus permeation. Other membrane configurations (e.g., hollow fiber) provide acceptable substitutes.

Sterile filtration may be added, as per Table 1, to eliminate bioburden. The final retentate will be filtered through a 0.22 micron modified polyvinylidene fluoride (PVDF) membrane (e.g. Millipore Millipak 200) using a filter loading of approximately $3×10^{13}$ $vp/cm^2$. In addition to modified PVDF, the sterile filter may be constructed of a variety of other materials that are well known in the art and available to the artisan. These may include but are not limited to polypropylene, cellulose, cellulose esters, nylon, polyethersulfone, or any other material which is consistent with low product binding. The filter may have a single membrane layer or may incorporate a prefilter of the same of different material. The product can be held frozen or at approximately 4 C for subsequent formulation and filling.

An orthogonal purification step may be added to deal with impurity clearance as well as an adventitious agent clearance. Orthogonal purification steps are not necessarily required and may be assessed by the skilled artisan and in turn implemented based on need. The concentration of the highest clinical dose, the robustness of impurity clearance, and cell substrate issues relating to tumorigenicity, adventitious viruses and prions all may define this need for the skilled artisan. Potential steps include flow-through cation exchange chromatography, reversed-phase adsorption, and hydroxyapatite chromatography. Flow-through cation exchange is particularly desirable because it should provide a high clearance factor for PrP and many potential adventitious viruses, including adeno-associated virus (AAV).

As noted herein, the present invention relates to purification of wild type, modified or recombinant virus. Of specific interest in gene vaccination and/or gene therapy applications is the use of a $1^{st}$ or $2^{nd}$ generation replication incompetent adenovirus, crippled by E1 or further deletions, including "gutless" adenovirus vectors. The adenovirus genome is generally associated with benign pathologies in humans, and the genomic organization of the virus has been well studied since its discovery in the early 1950s. In addition, the genome is amenable to manipulation, depending on the strategy utilized to construct the respective vector. A replication-incompetent virus (such as an E1/E3 deleted Ad5gag vector expressing a HIV gag transgene, as exemplified herein) requires a cell line which complements the deletions. Any such cell line may be used to generate recombinant virus vectors, with preferred, but not limiting, cell lines including 293 cells and PER.C6™ cells. To this end, numerous $1^{st}$ generation recombinant adenovirus vectors have been described in the literature (e.g., see Bett, et al., 1994, *Proc. Natl. Acad. Sci.* 91:8802-8806; WO 01/02607 and WO 02/22080). "Gutless" adenoviral vectors are a $2^{nd}$ generation adenoviral vector generally devoid of viral protein-coding sequences, frequently with viral proteins supplemented in trans by a helper virus (often an E1-deleted adenovirus) grown with the helper-dependent (HD) adenovector in a packaging cell line (e.g., PER.C6™). Absent viral proteins, these viral vectors can, in the alternative, be supplemented in trans by a cell line capable of expressing the structural and functional adenoviral proteins necessary for successful replication, packaging and rescue. In view of the increased popularity of these viral vectors and the ultimate need to prepare commercial scale quantities of either a viral vector based vaccine or gene therapy vehicle, it has become essential to develop more efficient qualitative and quantitative methodology for production of commercial grade recombinant adenovirus vectors. It will be understood that alternative serotypes, including but not limited to serotypes 2, 4, 12, 6, 17, 24, 26, 31, 33, 34 35, 36 and 16 are amenable purification via the large scale procedures disclosed herein. Adenoviral serotypes 2, 5 and 6, 24, 26, 35 and 36, particularly 5 are preferred for use in this invention, since at this point in time, more is known about these serotypes generally than other serotypes, and their complete DNA sequences are known. The prototype serotype 5 adenovirus has been completely sequenced (Chroboczek et al, 1992 *J. Virology* 186:280, which is hereby incorporated by reference.) They also belong to the subgroup C adenoviruses, which are not associated with human or rodent malignancies. However, as noted above, it is envisioned that any adenovirus serotype can be used in this invention, including chimeric (such as a 'switched' recombinant Ad virus, where say the E4 region of one serotype (e.g., Ad5) replaces the similar region of an alternative serotype (e.g., Ad24), which may allow for growth of the Ad24 chimeric virus in a cell line (e.g., PERC6) which expresses an Ad5 E1 region. In addition, non-human serotypes (e.g., adenovirus strains which infect chimpanzee) may also be purified by the methods disclosed herein. An exemplified, but in no way limiting, recombinant Ad5 vector is MRKAd5gag, as well as MRKAd5pol, both of which are disclosed in WO 02/22080.

Another related Ad vector is Ad5gag, as disclosed in WO 01/02607. Both of these PCT publications are hereby incorporated by reference.

The host cell for use in the method presented herein comprise any mammalian cell line which supports replication of the respective, especially any host cell line known in the art which will support infection and replication of a $1^{st}$ or $2^{nd}$ generation adenovirus vector. A preferred host cell is a host cell line which supports infection and replication of an E1 and/or and E1/E3 deleted recombinant adenovirus. As disclosed herein, such a replication-incompetent virus (such an Ad5gag, as exemplified herein) requires a helper cell line which complements the Ad5 E1 deletion. Any such cell line may be used to generate recombinant virus, with preferred, but not limiting, cell lines including 293 cells, PER.C6™ cells, 911 cells from a human embryonic retinal cell line (Fallaux et al. 1996, *Human Gene Therapy* 7: 215-222); E1-transformed amniocytes (Schiedner et al. 2000, *Human Gene Therapy* 11:2105-2116); an E1-transformed A549 cell line for a human lung carcinoma (Imler et al. 1996, *Gene Therapy* 3:75-84) and GH329: HeLa (Gao et al. 2000, *Human Gene Therapy* 11: 213-219). Such a cell line is transformed to support replication and packaging of a respective recombinant adenovirus, such as an E1 or E1/E3 deleted recombinant adenovirus. Additional cell lines which may be utilized in the present invention are again cell lines which have been adapted to act as host cells for a particular thermo-stable virus. It is preferable that the cell line be a continuous cell line and more preferable that the source of the cultured cells originate from a non-neoplastic tissue. It is also preferable that the source be mammalian, most likely from a primate origin, and especially of human origin. Again, a preferred cell line is a cell line which is useful for the propagation of an Ad E1 or E1/E3 deleted recombinant virus; a recombinant virus which compliment E1-deleted adenovirus vector included cell lines transfected with the gene encoding Ad E1 which have been selected for this transformed phenotype, such as 293 cells (epithelial cells from human kidney) and PER.C6™ (human embryonic retinoblasts). Other cell types include but are not limited to HeLa cells, A549 cells, KB cells, CKT1 cells, NIH/sT3 cells, Vero cells, Chinese Hamster Ovary (CHO) cells, or any eukaryotic cells which support the adenovirus life cycle.

Any upstream virus production process known in the art which can be adapted to large scale cell culture of mammalian host cells may be utilized to generate the starting material (i.e., a virus infected host cell culture which has be subjected to a post-infection period of culture growth so as to maximize the amount of intracellular and extracellular virus) for the purification methodology of the present invention, taking into account modifications known to the artisan as appropriate to account, for example, changes in cell density or the presence of microcarriers. This methodology is known in the art (e.g., see U.S. Pat. No. 6,194,191 for a review of cell culture techniques known in the art, as well as "Culture of Animal Cells: A Manual of Basic Techniques", 2000, Ed. R. I. Freshney, Wiley-Liss, both documents which are hereby incorporated by reference) and can be adapted from virus to virus and site to site in order to optimize virus production. For example, PER.C6™ cells may be cultured in a 300 L bioreactor with 240 L working volume and infected with a recombinant Adenovirus encoding a HIV transgene gag (such as MRKAd5gag or Ad5gag) at a viable cell concentration of $0.59 \times 10^6$ cells/ml at a multiplicity of infection (MOI) of 280 vp/cell. Approximately fifty hours post-infection (hpi), the bioreactor, at a total cell concentration of approximately $0.55 \times 10^6$ cells/ml with 55% viability, is harvested. At the time of the start of this unit operation, approximately 25% of the virus is the supernatant, as per an AEX assay. Similarly, PER.C6™ cells are cultured in 20 L Wave Bioreactors with a 10 L working volume and infected with a recombinant Adenovirus vector encoding a HIV transgene nef at a multiplicity of infection (MOI) of about 290 viral particles per cell (vp/cell) and a viable cell concentration of about $0.72 \times 10^6$ cells/ml. Approximately fifty hours post infection (hpi), two wave bioreactors at a total cell concentration of approximately $0.66 \times 10^6$ cells/ml with 81% viability are harvested. At the time of the start of concentration, 20.4% of the virus was in the supernatant per anion exchange AEX assays.

The following non-limiting Examples are presented to better illustrate the invention.

EXAMPLE 1

AEX Chromatography without a Selective Precipitation Step

Figure 2A:
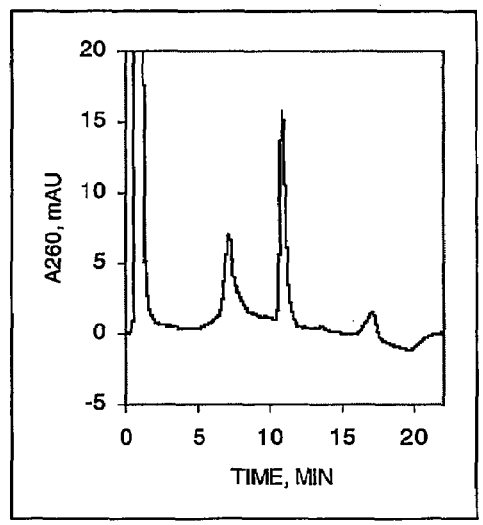
FIGS. 2A, 2B and 2C show results from anion exchange assay chromatograms for the preparative AEX chromatography step. (A) feed; (B) flowthrough; (C) product pool. Peak IDs are as follows: 1 minute—misc. impurities, PS-80; 7 minutes—hexon protein; 11 minutes—AdV particles; 16 minutes—nucleic acid.
Figure 2B:
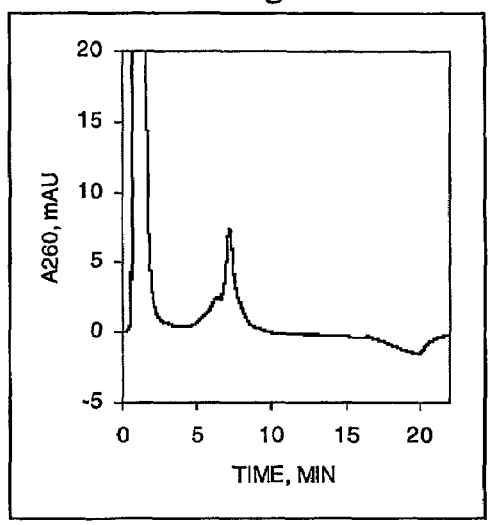
Figure 2C:
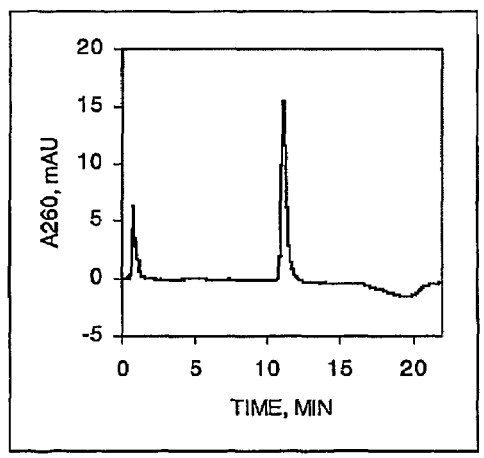

An anion exchange (AEX) chromatography with certain resin selection and column operating conditions (NaCl concentration and pH) allow for high capacities of virus loading. It is also shown herein that inclusion of a detergent (e.g. PS-80) in the running buffers inhibit aggregations during loading and elution. Overall, it is disclosed herein that AEX resin utilization as practiced will improve 5-20 fold over the previously reported methods, with usable capacity demonstrated (but not necessarily limited) to $2.0 \times 10^{13}$ vp/mL resin. Crucial to the implementation of an economically efficient and robust process are the choice of resin with a high dynamic capacity for adenovirus and methodologies to ensure that the capacity can be utilized without product aggregation. Three significant advances address these issues: (1) Source 15Q (Amersham Biosciences) has been selected for its high capacity—other resins including Source 30Q (Amersham Biosciences) and Fractogel TMAE (EM Industries) also provide acceptable results though with lower capacities which are likely caused by lower effective surface area to volume ratios; (2) PS-80 has been added to the running buffers at 0.1% to prevent aggregation; and (3) the product is loaded at a conductivity which is sufficiently high to ensure that free adenovirus hexon and chromatographically similar impurities do not bind to the resin. For example, loading at a conductivity of 38 mS is approximately equivalent to 0.38 M NaCl. The salt concentration is suitable to bind adenovirus particles but not related impurities; this translates into a higher binding capacity for adenovirus. The optimal conductivity will depend on the adenovirus serotype (e.g., Adenovirus Type 6 should be loaded at approximately 0.33 M NaCl since this concentration allows free hexon to remain non-bound but allows the viral particles to bind readily). These conditions result in a step which operates significantly more efficiently than other conditions reported. FIG. 1 shows how this procedure operates. For illustrative purposes, a preparative chromatogram is shown using the procedure described on a stream which has not undergone selective precipitation. Instead, the clarified lysate had been treated with high levels of nuclease. In addition, the feed (FIG. 2A), flowthrough (FIG. 2B), and eluate (FIG. 2C) of the preparative run are shown on a 10 volume gradient from 0.3-0.6 M NaCl in FIGS. 2A-C. It is apparent that by using this approach, the peak comprised predominantly of adenovirus hexon can be moved to the flow-through thereby eliminating any competition for binding and significantly improving the resolution of adenovirus from these impurities and the column capacity. The anion exchange product then can be diafiltered into formulation buffer and sterile filtered. Alternatively, an additional chromatography step (e.g. cation exchange) may be added either before or after the diafiltration with the potential to improve the robustness of impurity and/or virus/prion clearance.

EXAMPLE 2

Purification of MRKAd5gag Adenoviral Vector from Host Cell Lysate

Approximately 12.5 Liters of MRKAd5gag Triton-lysed material (lot 0114) was obtained from a 300 L bioreactor run and split into 9.5 and 3-L aliquots. The aliquots were precipitated separately in 20-Liter Nalgene beakers. Mixing parameters for each aliquot were specified by scaling down reasonable 1000 L precipitation conditions by maintaining a constant volumetric turnover time. Both aliquots were precipitated by adding DB to a final concentration of 0.0435% wt./vol using a concentrated solution (2% DB in 40 mM NaCl). Addition rate of this mixture was 0.3 mL/min for each liter of lysate. The DB solution was added sub-surface. The use of sub-surface addition is supported by data generated by the inventors.

Once the precipitation was complete, depth filtration was conducted sequentially on each aliquot using the same filtration apparatus. Clarification was conducted using a Millipore Opticap CE-25 filter in series with a Millipore Opticap DE-45. Both filters provide filtration surface areas of 1 ft$^2$. All 12.5-Liters of precipitated material was processed successfully with a maximum pressure build up in each filter of 1 psi. Following clarification the turbidity was reduced from approximately 540 to 3.6 NTU. As shown in Table 2, the yield across this step was only 60% but appeared to be caused by an adsorption phenomena and was therefore exacerbated by the low throughput used in this example.

Only 9.5 Liters of this material was processed through to final product. Concentration and diafiltration were performed using a 0.1 m$^2$ 500 kDa NMWCO PES ultrafilter (Millipore Pellicon 2). This membrane was incorporated into a TFF apparatus containing a membrane filter housing and a lobe pump. A concentration factor of 20 was performed on the clarified material to decrease total batch volume. After concentration, BENZONASE™ was added at 15 U/mL material and the batch was slowly recirculated in the system for two hours with the permeate line closed. After incubation the batch was diafiltered against 5 volumes of 50 mM HEPES, 2 mM MgCl$_2$, 1 M NaCl, pH 7.5.

Figure 3:
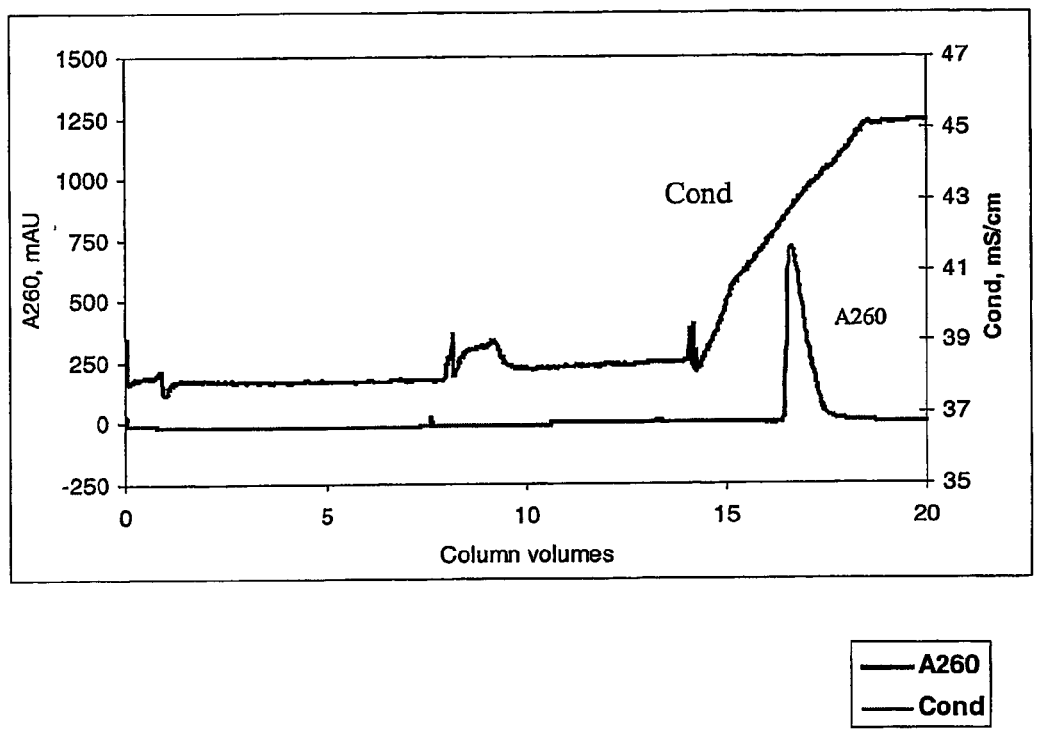
FIG. 3 shows a preparative anion exchange profile for Example 2. Loading, washing, and elution are shown.

Anion exchange chromatography was performed at a loading of 2.4×10$^{12}$ vp/mL resin. The pressure drop across the column did not increase during loading indicating that the stream was essentially free of debris and fouling agents. In addition, almost no UV absorbance (at 260 or 280 nm) was seen during product loading, washing, or following product elution (FIG. 3). These observations demonstrate that the bulk of the impurities were removed upstream of anion exchange chromatography and are consistent with the impurity data below.

The second ultrafiltration was performed using five 50 cm$^2$, 500 kD PES membranes. Five diafiltration volumes were conducted to exchange the virus into the formulation buffer. As shown in Table 2, the yield across this step was low but likely caused by virus permeation and/or low membrane loading. The product was then sterile filtered with a 10 cm$^2$ Millipore Sterivex GV 0.22 micron filter. No pressure build-up was seen during the sterile filtration which suggests a lack of aggregated virus. Note that the actual process yields are conservative since they do not take into account substantial sampling for analytical purposes.

TABLE 2

Yield Table for MRKAd5gag

| Sample | Volume (mL) | AEX (vp/mL) | Viral Particles | Step Yield | Net Yield |
|---|---|---|---|---|---|
| Lysate A | 9475 | 8.68 × 10$^{10}$ | 8.23 × 10$^{14}$ | | |
| Lysate B | 3045 | 6.12 × 10$^{10}$ | 1.86 × 10$^{14}$ | | |
| Total | 12520 | | 1.01 × 10$^{15}$ | 100% | 100% |
| DB ppt. A[1] | 9655 | 9.15 × 10$^{10}$ | 8.84 × 10$^{14}$ | | |
| DB ppt. B | 3094 | 6.26 × 10$^{10}$ | 1.94 × 10$^{14}$ | | |
| Total | 12749 | | 1.08 × 10$^{15}$ | 107% | 107% |
| Clarified Lysate A[2] | 9553 | 3.75 × 10$^{10}$ | 3.59 × 10$^{14}$ | | |
| Clarified Lysate B | 3279 | 8.89 × 10$^{10}$ | 2.91 × 10$^{14}$ | | |
| Total | 12833 | | 6.50 × 10$^{14}$ | 60% | 65% |
| UF1 Retentate | 263.3 | 1.19 × 10$^{12}$ | 3.14 × 10$^{14}$ | | |
| UF1 Wash | 189.4 | 3.22 × 10$^{11}$ | 0.61 × 10$^{14}$ | | |
| Total | 452.7 | | 3.75 × 10$^{14}$ | 105% | 68% |
| Anion Exchange Pool[3] | 205.4 | 1.47 × 10$^{12}$ | 3.01 × 10$^{14}$ | 80% | 54% |
| UF2 Retentate | 276.2 | 7.17 × 10$^{11}$ | 1.74 × 10$^{14}$ | 69% | 38% |
| Sterile Filtered Product | 231 | 7.10 × 10$^{11}$ | 1.64 × 10$^{14}$ | 94% | 36% |

[1]Precipitate filtered through 0.45 micron syringe filter before assay
[2]Only clarified lysate A processed forward in this example
[3]Only 166 mL of AEP was forwarded to the second ultrafiltration Protein and DNA clearance data are illustrated in Table 3. Note that the residual DNA levels are below the limit of quantitation of the assay after anion exchange indicating that the exemplified process has substantial process robustness. Specific protein levels do not change from the UF1 product to final product and are near the theoretical levels for adenovirus. This observation is quite consistent with the lack of UV signal displayed in the preparative AEX flow through and wash. The enhanced "clean-up" of the stream through precipitation and clarification is believed to be the primary cause of this improvement. Table 3 also shows that infectivity is maintained across the process.

TABLE 3

Infectivity and Impurity Clearance Data from MRKAd5gag Purification

| Intermediate | Residual DNA, pg/10$^{11}$ vp | Protein (BCA) µg/10$^{11}$ vp | AEX/QPA, vp/IU |
|---|---|---|---|
| Lysate | 5.52e6 | 1292 | — |
| DB ppt | 4.30e5 | 811 | — |
| Clar Lysate | — | 1802 | — |
| UF1 FR | 229 | 14 | 19 |
| AEP | 2.0 (<5) | 13 | 19 |
| UF2 FR | — | 16 | — |
| SFP | 2.2 (<5) | 15 | 16 |

EXAMPLE 3

Cationic Surfactants for Precipitation of Nucleic Acid Molecules

Alternative surfactants were studied to investigate the relative specificity of different types of cationic detergents. This example provides for additional understanding of DB's increased selectivity. Table 4 contains the list of surfactants used in this example along with their formula weights and corresponding molecular structures.

TABLE 4

Structural Differences of Cationic Detergents

| Surfactant | Acronym | Formula Weight (D) | Structure |
|---|---|---|---|
| Hexadecyl-trimethyl-ammonium bromide | CTAB | 365 | $H_3C-N^+(CH_3)_2-C_{15}H_{31}$, $Br^-$ |
| Tetradecyl-trimethyl-ammonium chloride | TTA | 336 | $H_3C-N^+(CH_3)_2-C_{13}H_{31}$, $Cl^-$ |
| Cetylpyridinium chloride | CPC | 340 | pyridinium-$C_{15}H_{31}$, $Cl^-$ |
| Domiphen bromide | DB | 414 | phenyl-$O-CH_2CH_2-N^+(CH_3)_2-C_{12}H_{25}$, $Br^-$ |
| Benzethonium chloride | BTC | 448 | $(H_3C)_3C-C(CH_3)_2$-phenyl-$O-CH_2CH_2-O-CH_2CH_2-N^+(CH_3)_2-CH_2$-phenyl, $Cl^-$ |

Figure 4:
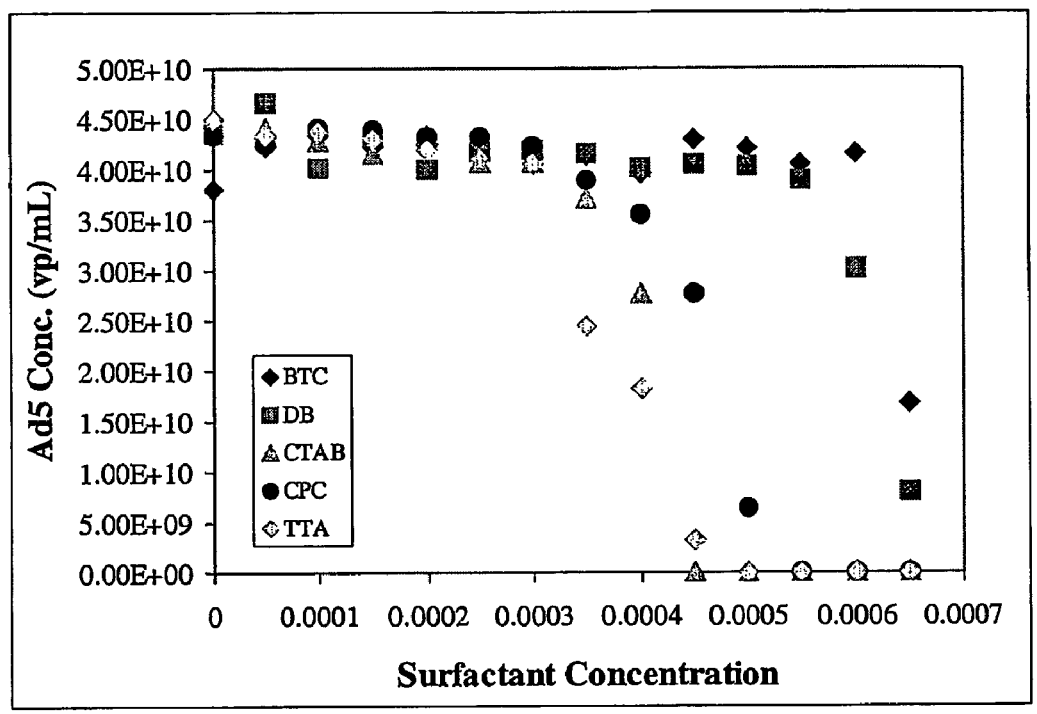
FIG. 4 shows adenovirus precipitation profiles for cationic detergents BTC, DB, CTAB, CPC and TTA.
Figure 5:
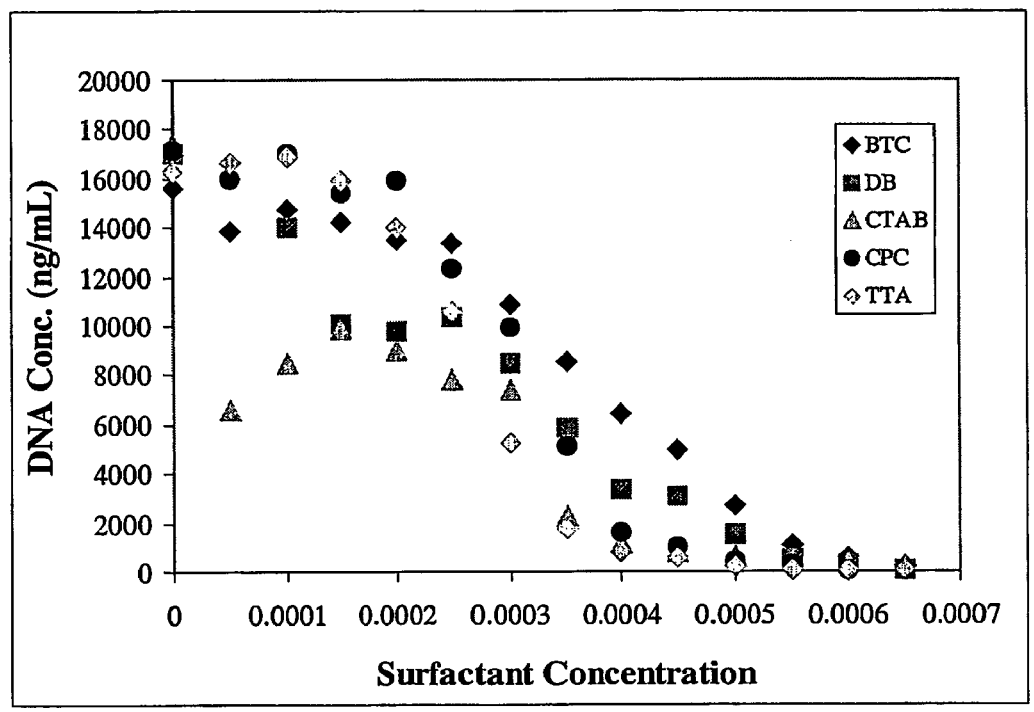
FIG. 5 shows the DNA precipitation profiles for cationic detergents BTC, DB, CTAB, CPC and TTA.

Aliquots of 1-mL of cell lysate were treated with a range of concentrations of surfactants and vortexed immediately. Following filtration with 0.45-micron syringe filters, samples were analyzed for DNA concentration via the Picogreen (Molecular Probes) assay and the adenovirus concentration was determined using an anion exchange HPLC assay. FIG. 4 displays the adenovirus precipitation profiles. A shorter chain length (e.g., CTAB verses TTA) displays a more distinct precipitation profile. Although 0.03% is the maximum allowable surfactant concentration prior to adenovirus precipitation for both CTAB and TTA; the DNA profiles differ (see FIG. 5). In comparing the DB and BTC precipitation profiles they were found to be nearly identical. Although, when moving back off the edge at which adenovirus precipitation begins, the selectivity for DNA is higher for DB than BTC at all concentrations (see FIG. 5). That is, contact between BTC's positively charged nitrogen and the DNA's phosphorus group may be sterically hindered by the closer proximity of the benzene ring in BTC. A result of the charge being shielded or lack of a distinct hydrophobic tail may also be to blame. It can be concluded, however, that ringed structures are more robust and selective for DNA. The proposed hydrophobic interaction could be the driving force for this phenomenon. A single yet significant difference between the CPC and CTAB molecules is the presence of a pyridinium ring. The positive charge is distributed throughout this ring. As seen in FIG. 5 the initial precipitation of adenovirus by CPC and CTAB begins at 0.03%. Moreover the precipitation profile is much less aggressive when the positive charge is distributed. However, as also shown in FIG. 5, CTAB precipitates more DNA across a majority of surfactant concentrations.

EXAMPLE 4

Figure 6:
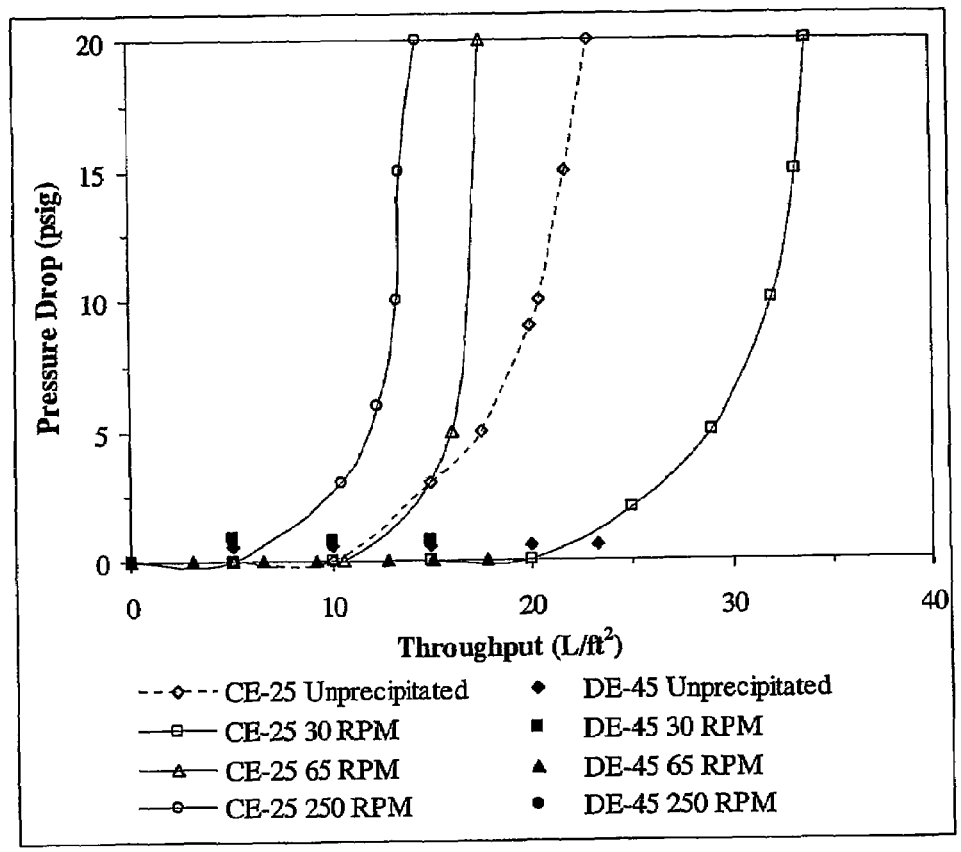
FIG. 6 shows various capacities for a CE-25 and DE-45 depth filtration under various mixing conditions.

Effects of Mixing Speed on Depth Filtration of Precipitated Adenovirus Preparations Domiphen Bromide (DB) precipitation of DNA in the PERC.6™ lysate is sensitive to mixing conditions. The performance of depth filtration for different mixing conditions generated by different impeller speed is evaluated in this Example. MRKAd5gag0114 was precipitated at various impeller speeds of 30, 65, and 250 RPM. Clarification consisted of a two-stage depth filtration. The precipitates were first filtered using a CE-25 Millipore Millistak +50 (0.02 ft$^2$) at 9 L/hr/ft$^2$. The material was pooled and filtered using a DE-45 Millipore Millistak +50 (0.02 ft$^2$) at the same flow rate. The pressure drops as a function of throughput for the various mixing conditions are compared to the control prior to precipitation in FIG. 6. The 30 RPM mixing showed a significant increase in throughput for the CE-25 filter at 20 psig as compared to the control case, but showed greater losses in overall yield relative to the 65 and 250 RPM mixing conditions. The other mixing conditions showed lower throughputs than the control case for the CE-25 filter, but showed higher yields overall between precipitation and depth filtration than the control case. The dependence of clarification on mixing conditions underlines the importance of re-optimization after the mixing conditions have been determined. As for the throughput of the DE-45, little pressure (<1 psi) build-up was observed in all of the suspensions examined. Thus since the DE-45 never came close to its capacity, the CE-25 filter is the limiting factor in the clarification scheme. Although the CE-25 filters reduced the turbidity to varying amounts, as seen in Table 5, the following DE-45 filters reduced the turbidity of the precipitated lysates to less than 6 NTU, while only reducing the turbidity of the unprecipitated lysate to 10.

TABLE 5

Turbidity Reduction for Various Precipitation Conditions

| | | Mixing Rate | | |
|---|---|---|---|---|
| Parameter | Unprecipitated | 30 RPM | 65 RPM | 250 RPM |
| Feed (NTU) | 41 | 237 | 200 | 600 |
| CE25 pool (NTU) | 14 | 22 | 24 | 4.4 |
| Reduction | 66% | 91% | 88% | 99% |
| DE45 pool (NTU) | 10 | 5.2 | 4.8 | 2.2 |
| Reduction | 29% | 76% | 80% | 50% |

EXAMPLE 5

Recombinant Adenovirus Preparation from 300 Liter Bioreactor

A 240-L scale cell culture was performed in the 300-L bioreactor. This lot confirmed the scalability of the purification process with individual unit operations run at the equivalent of 60 to 214 liters of cell suspension. The overall process yield was 54% as measured by anion exchange HPLC. The infectivity ratio (vp/IU) and specific DNA content of the final product were (31 vp/IU) and (<16.5 pg/$10^{11}$ vp), respectively, and were comparable to historical data.

Lysis—Lysis was completed by the addition of concentrated buffers to achieve final concentrations of 0.1% Triton X-100 and 0.05% Polysorbate-80. The lysate was held overnight at room temperature prior to the detergent precipitation step.

Precipitation—DNA precipitation was performed at 214 L scale in the bioreactor. A solution of 0.5% domiphen bromide with 40 mM NaCl was added above surface over approximately two hours to a final concentration of 0.04% domiphen bromide. The agitator was operated at 80 rpm during this time. Agitation speed was selected by operating at a volumetric turnover time which had been demonstrated as effective at smaller scale and that could be implemented at larger scale. After precipitation, approximately 153 kg of precipitated lysate was transferred for depth filtration.

Depth Filtration—The precipitated lysate was clarified with a two-stage depth filtration scheme. For this run, twelve inch Millistak cartridges were used with a 6.8 square foot CE20 filter followed by a 6.8 square foot CE-50 filter. Filtration was conducted at a constant flow rate of 2 L/min and 144.2 kg of clarified lysate was recovered. The overall yield was 84%.

Ultrafiltration—Approximately 60 L of clarified lysate were concentrated 20-fold with 0.3 m² of membrane area (Millipore Pellicon II 500 kDa PES). The recirculation rate was maintained at 1 L/min and permeate flux was controlled at 0.3 L/min. Nuclease digestion was performed by the addition of 15 U/mL BENZONASE™ followed by two hours of incubation at room temperature. Next, the buffer was exchanged with 5 diafiltration volumes of 50 mM HEPES, 2 mM MgCl$_2$, 1 M NaCl, pH 7.5 for impurity clearance. The product was held overnight at 4 C.

Anion Exchange Chromatography—The UF1 product was diluted to a conductivity of 38 mS/cm using 50 mM HEPES, 2 mM MgCl$_2$, 0.1% PS-80, pH 7.5. A 10 cm diameter FineLine column (Amersham Biosciences) was packed with a total of 863.5 mL of Source 15Q resin (Amersham Biosciences). Product was loaded at a linear velocity of 1.5 cm/min, washed with 5 column volumes of 50 mM HEPES, 2 mM MgCl2, 0.39 M NaCl, 0.1% PS-80, pH 7.5 and then eluted during a four column gradient to 0.47 M NaCl.

Ultrafiltration—The product peak was diluted and adjusted to an adenovirus concentration of approximately $1.05 \times 10^{12}$ vp/mL and a salt concentration of 1 M NaCl. The batch was diafiltered into formulation buffer (5 mM Tris, 75 mM NaCl, 1 mM MgCl2, 5% sucrose, 0.005% PS-80, pH 8.0) via 0.1 m² 500 kDa PES membrane (Millipore Pellicon II Biomax). The permeate flux was maintained at 80 mL/min.

Sterile Filtration—The ultrafiltration retentate was sterile filtered with a Millipore Millipak-20 filter (100 cm²) at a constant feed flow rate of 150 mL/min.

Table 6 shows the step and net yields of MRKAd5gag. This lot produced 1.91E15 viral particles with an overall net yield of 54%. Note that in several instances the input to a step is significantly less than the output of the prior step due to sampling.

TABLE 6

MRKAd5gag Yield Table

| Sample | Vol, mL | AEX, vp/mL | Ad, vp | Step Yield | Net Yield |
|---|---|---|---|---|---|
| Lysate | 214200 | $6.40 \times 10^{10}$ | $1.37 \times 10^{16}$ | | |
| Precipitate[1] | 232850 | $5.08 \times 10^{10}$ | $1.18 \times 10^{16}$ | 86% | 86% |
| Depth Filtration feed | 152906 | $5.08 \times 10^{10}$ | $7.77 \times 10^{15}$ | | |
| Clarified Lysate | 144224 | $4.70 \times 10^{10}$ | $3.39 \times 10^{15}$ | 85% | 73% |
| UF1 feed | 59885 | $5.08 \times 10^{10}$ | $3.04 \times 10^{15}$ | 108% | 79% |
| UF1 retentate | 2925 | $9.82 \times 10^{11}$ | $2.87 \times 10^{15}$ | | |

TABLE 6-continued

MRKAd5gag Yield Table

| Sample | Vol, mL | AEX, vp/mL | Ad, vp | Step Yield | Net Yield |
|---|---|---|---|---|---|
| UF1 wash | 501 | $5.58 \times 10^{10}$ | $2.79 \times 10^{15}$ | | |
| UF1 Total | 3429 | $8.46 \times 10^{11}$ | $2.90 \times 10^{15}$ | 96% | 75% |
| AE feed | 8357 | $3.37 \times 10^{11}$ | $2.81 \times 10^{15}$ | 97% | 73% |
| AE Product | 1198 | $1.77 \times 10^{12}$ | $2.12 \times 10^{15}$ | 75% | 55% |
| Diluted AEP[2] | 2000 | $1.05 \times 10^{12}$ | $2.10 \times 10^{15}$ | | |
| UF2 feed[2] | 1900 | $1.05 \times 10^{12}$ | $1.99 \times 10^{15}$ | | |
| UF2 retentate | 1876 | $1.05 \times 10^{12}$ | $1.97 \times 10^{15}$ | 99% | 55% |
| SF feed | 1864 | $1.05 \times 10^{12}$ | $1.96 \times 10^{15}$ | | |
| Sterile-filtered product | 1935 | 9.95E+11 | 1.92E+15 | 98% | 54% |

Figure 7:
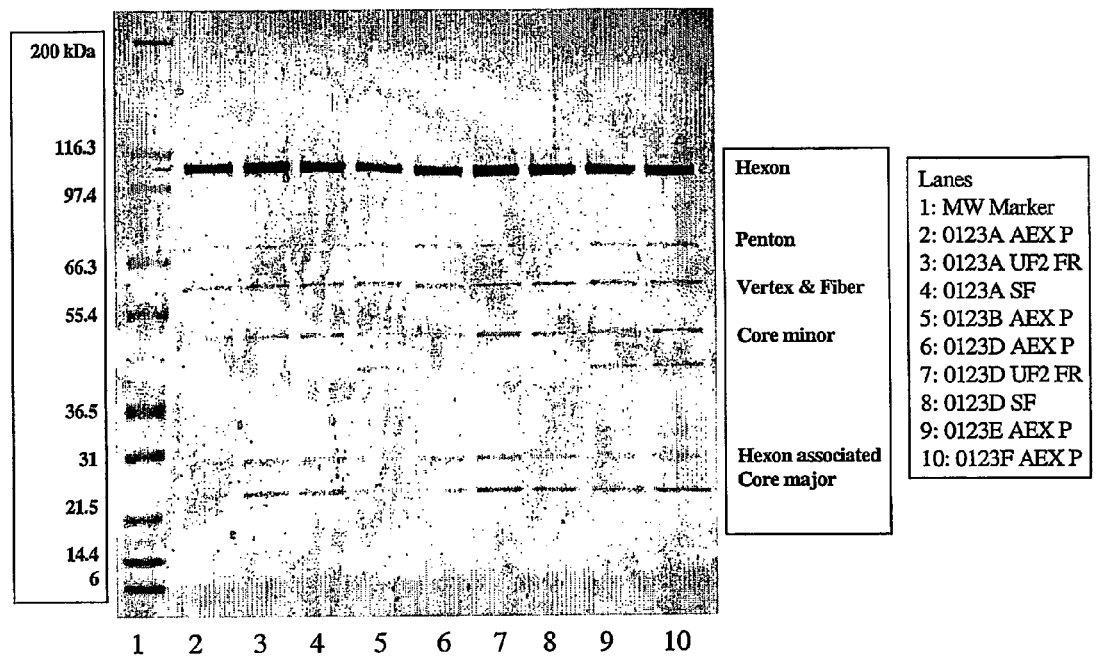
FIG. 7 shows an SDS-PAGE analysis of a step-by-step adenovirus (MRKAd5gag) purification procedure from a 300 liter cell culture. Loading was normalized to 6.34E9 vp.

[1]Filtered through 0.45 micron PVDF syringe filter prior to assay
[2]Calculated value FIG. 7 shows analysis by SDS-PAGE of the exemplified lot as well as some additional experiments which are not described herein. Lanes 2-4, in particular, show process intermediates from this example and demonstrate the high purity of the product since all significant bands are identified as adenovirus structural proteins.

Table 7 summarizes the DNA removal for the lot. Over 2 logs of DNA reduction was achieved by precipitation and depth filtration. Again, levels at or near the limit of detection of the assay are achieved. Table 7 also presents the detergent clearance profile during this exemplified run. The detergents were both effectively cleared in anion exchange and the second ultrafiltration. The amount of detergent in the product stream was reduced to below the assay detection limit (approximately 0.001%) after UF2.

TABLE 7

Impurity removal during lot MRKAd5gag0123A

| Intermediate | DNA (QPCR) (pg/10^11 vp) | Triton (%) | DB (%) |
|---|---|---|---|
| Lysate | $1.9 \times 10^7$ | 0.109 | <0.001% |
| Clarfied lysate | $8.3 \times 10^4$ | 0.078 | 0.011 |
| UF1 product | 3410 | 0.297 | 0.122 |
| AEP | 30 | 0.007 | 0.008 |
| UF2 retentate | <5 | <0.001% | <0.001% |
| Sterile-filtered product | 5 | <0.001% | <0.001% |

EXAMPLE 6

CTAB Precipitation Vs. High Nuclease Use

MRKAd5gag was utilized to compare a process incorporating CTAB precipitation and no nuclease treatment (arm C) with a process which utilized high nuclease levels (150 U/mL BENZONASE™, 150 U/mL RNase) but no precipitation (Arm A). Table 8 contains the residual DNA clearance data for both purification arms. Note that the CTAB precipitation reduces the overall DNA earlier in the process while the base case achieves the majority of its clearance through the nuclease treatment (UF1 CR to UF1 DR). DNA levels in the Anion Exchange Product (AEP) are within assay variability. These data show that a detergent-based precipitation step may replace a high concentration nuclease treatment entirely without an impact on product quality.

TABLE 8

Residual DNA
Results of BENZONASE™ Digestion
verses DNA Precipitation via CTAB

| Process Intermediate | MRKAd5gag0112A Residual DNA (pg/1E11 vp) | MRKAd5gag0112C Residual DNA (pg/1E11 vp) |
|---|---|---|
| Lysate | $9.87 \times 10^7$ | $9.87 \times 10^7$ |
| Clarified Lysate | $7.25 \times 10^6$ | $1.10 \times 10^6$ |
| UF1 Concentration Retentate | $1.01 \times 10^7$ | — |
| UF1 Retentate | $2.58 \times 10^3$ | $5.38 \times 10^5$ |
| AEP (Anion Exchange Product) | 595 | 260 |

EXAMPLE 7

CPC and Domiphen Bromide Precipitation

In this example, processes utilizing CPC or DB precipitation (with no nuclease use) are compared to a high nuclease control. In particular, the following purification scenarios are compared:

0113A: No precipitation, BENZONASE and RNase at 150 U/mL each, AEX loading at approximately $5 \times 10^{12}$ vp/mL 0113C: Precipitated with CPC, no nuclease use, AEX loading at approximately $5 \times 10^{12}$ vp/mL 0113D: Precipitated with DB, no nuclease use, AEX loading at approximately $5 \times 10^{12}$ vp/mL Step yields were comparable across the three arms except for unusually low UF1 yields in arm A (see Table 9).

TABLE 9

Yield Table for MRKAd5gag0113

| STEP | 0113A1 | 0113C | 0113D |
|---|---|---|---|
| PPT | | 102% | 100% |
| CL | 83% | 84% | 93% |
| UF1 FR | 60% | 109% | 110% |
| AEP | 76% | 88% | 80% |
| NET | 38% | 82% | 82% |

Residual DNA data for the lot are listed in Table 10. These data suggest a high overall efficiency for the precipitation-based processes even in the absence of any nuclease use. The anion exchange product was not processed through UF2 in this example, so final product values are not available.

TABLE 10

DNA Clearance for MRKAd5gag0113

| Intermediate | Residual PER.C6 DNA, pg/1e11 vp | | |
|---|---|---|---|
| | 0113A | 0113C | 0113D |
| LYS | $8.20 \times 10^6$ | $8.20 \times 10^6$ | $8.20 \times 10^6$ |
| UF1 retentate | 116 | 4.88e5 | 4.98e5 |
| AEP | 8.7 | 59 | 26 |

Protein clearance is shown in Table 11 below. The efficiency of protein removal in the UF1 step appears to be significantly improved prior to precipitation, but purity differences at the AEP step cannot be discerned using total protein since the vast majority of protein present is the product. As a result, relative protein impurity for the AEPs is addressed by SDS-PAGE analysis in Example 8.

TABLE 11

Total Protein Clearance for MRKAd5gag0113 lots (BCA Assay)

| Intermediate | 0113A $\mu g/10^{11}$ vp | 0113C $\mu g/10^{11}$ vp | 0113D $\mu g/10^{11}$ vp |
|---|---|---|---|
| LYS | 1370 | 1255 | 1450 |
| CL | 1201 | 1183 | 1210 |
| UF1 DR | 228 | 66 | 113 |
| AEP | 15 | 13 | 13 |

While CTAB was shown to not have an effect on adenovirus infectivity (lot 0112), structural differences and possible mechanism differences of CPC and DB precipitation warranted additional infectivity data. For these three purifications, the ratio of viral particles to infectious units was as follows: A-26 vp/IU; C-32 vp/IU; D-29 vp/IU. These ratios are statistically equivalent and demonstrate that the procedures outlined herein do not impact product infectivity.

EXAMPLE 8

SDS-PAGE Analysis for Lots MRKAd5gag0112, MRKAd5gag0113 and MRKAd5gag0114

Figure 8:
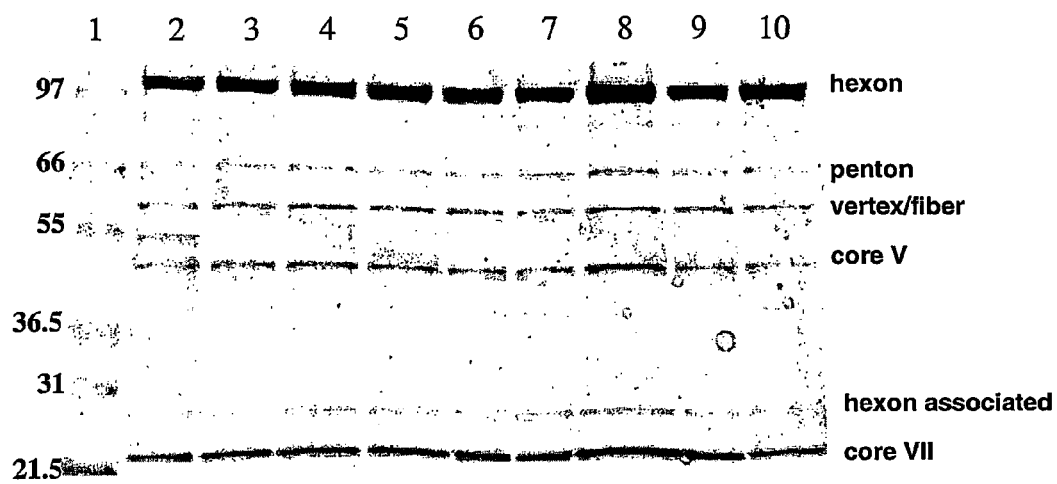
FIG. 8 shows SDS-PAGE gel protein analysis at the anion exchange product (AEP) intermediate for three exemplified adenovirus preparations. All samples loaded at 1.19e10 total vp. Lane (1) MW markers; (2) 0112A; (3) 0112C; (4) 0114; (5) 0113A1; (6) 0113A2; (7) 0113A3; (8) 0113B; (9) 0113C; (10) 0113D.

SDS-PAGE gel protein analysis was performed on in-process samples from development purification lots MRKAd5gag0112, MRKAd5gag0113 (Example 7), and MRKAd5gag0114 (Example 2), as shown in FIG. 8. Several important observations can be made. First, incorporating CTAB precipitation (0112C, lane 3) appears to lead to higher protein purity at the Anion Exchange Product (AEP) than the control arm (0112A, lane 2). Second, lanes 5-10 show similar purity for the AEP despite the following process variations: (a) AEX loading at 5, 10, and $15 \times 10^{12}$ vp per mL resin with 150 U/mL BENZONASE™ treatment and no precipitation (0113A1-A3-lanes 5-7); (b) use of only 5 U/mL BENZONASE without precipitation (0113B-lane 8); (c) CPC or DB precipitation without nuclease use (0113C & D-lanes 9 and 10). Third, the AEP from lot 0114 (lane 4), which incorporated both DB precipitation and low-level BENZONASE use, shows better protein purity (e.g. less 39- and 50-kDa impurities).

EXAMPLE 9

600 Liter Scale Purification of Adenovirus Type 5

The process was further scaled up, beginning with 600 L of cell lysate. The process specifics used are similar to those described in Example 5, but include the following differences: (1) depth filtration was performed with a Millipore CE20 filter followed by a CUNO CP50 filter (incorporates positive charge) in a 2:1 area ratio, (2) 300 kDa ultrafilters were used, (3) 0.1% PS-80 is included in the diafiltration buffer, and (4) a recombinant adenovirus subjected to purification was MRKAd5pol, which is described in detail in PCT publication WO 02/22080.

Yields for this process are shown in Table 12. Infectivity of the final product was confirmed by a $TCID_{50}$ assay, with an infectivity ratio of 4 vp/IU. The mean particle size by Dynamic Light Scattering was 123 nm, consistent with theoretical expectations. Specific residual DNA levels, total protein levels, and process residuals are shown in Table 13. These data further confirm the scalability of this process.

TABLE 12

MRKAd5pol Yield Table For 600-L Scale Purification

| Sample | Vol, L | AEX, vp/mL | Ad, vp | Step Yield[2] | Net Yield |
|---|---|---|---|---|---|
| Lysate | 615 | $2.62 \times 10^{10}$ | $1.61 \times 10^{16}$ | — | — |
| Precipitate[1] | 668 | $2.32 \times 10^{10}$ | $1.55 \times 10^{16}$ | 96% | 96% |
| Clarified Lysate | 672 | $1.83 \times 10^{10}$ | $1.23 \times 10^{16}$ | 80% | 77% |
| UF1 Product | 30.6 | $3.53 \times 10^{11}$ | $1.08 \times 10^{16}$ | 93% | 71% |
| AE Product | 2.64 | $3.55 \times 10^{12}$ | $9.37 \times 10^{15}$ | 89% | 64% |
| UF2 Product | 11.3 | $7.22 \times 10^{11}$ | $8.16 \times 10^{15}$ | 92% | 59% |
| Sterile-Filtered Product | 10.3 | $7.10 \times 10^{11}$ | $7.31 \times 10^{15}$ | 98% | 58% |

[1]Filtered through 0.45 micron PVDF syringe filter prior to assay
[2]Step yields take into account large samples taken of process intermediates (includes precipitate: 2.2 L; clarified lysate: 37.3 L; UF1 product: 0.8 L; AE Product: 0.15 L; UF2 Product: 1.0 L)

TABLE 13

Impurity Clearance During 600-L Scale Purification

| Sample | DNA (QPCR) pg/$10^{11}$ vp | Protein (BCA), ug/$10^{11}$ vp | Triton % | DB % |
|---|---|---|---|---|
| Lysate | 3.5E+07 | 2313 | 0.134 | — |
| Clarified Lysate | 8.4E+04 | 2404 | 0.082 | 0.021 |
| UF1 Product | 736 | 114 | 0.113 | 0.031 |
| AE Product | 20 | 9 | 0.003 | 0.003 |
| UF2 Product | 17 | 8 | <0.0012 | <0.0008 |
| Sterile-Filtered Product | 14 | 8 | <0.0012 | <0.0008 |

EXAMPLE 10

Adenovirus Type 6

In this example, adenovirus type 6 (from subgroup C) is purified. Process changes in this example are predominantly in the preparative anion exchange chromatography step. There, the UF1 product was diluted to approximately 30.7 mS/cm and loaded on to the Source 15Q resin. The column was washed with a buffer containing 0.32 M NaCl. Product elution occurred across a four column volume gradient to a final NaCl concentration of 0.41 M. Otherwise, the process was run essentially as described in Example 9.

Yields from this purification demonstrate that process performance is comparable to Ad5 (Table 14). Specifically, residual DNA levels by Q-PCR were reduced by over 2 logs following precipitation and clarification. Levels are reduced to 3 pg/$10^{11}$ vp in the product. Specific total protein values (Table 15) also indicate that the vast majority of the total protein is removed by the end of UF1 and the residual impurities are normalized following AEX. As seen with adenovirus type 5 this data indicates that adenovirus types in the same subgroup may be purified.

TABLE 14

Ad6 Yield Table For 20-L Scale Purification

| Sample | Vol, mL | AEX, vp/mL[2] | Ad, vp | Step Yield[2] | Net Yield |
|---|---|---|---|---|---|
| Lysate | 3664 | $1.06 \times 10^{11}$ | $3.88 \times 10^{14}$ | — | — |
| Precipitate[1] | 3952 | $1.01 \times 10^{11}$ | $3.99 \times 10^{14}$ | 103% | 103% |
| Clarified Lysate | 3898 | $8.71 \times 10^{10}$ | $3.40 \times 10^{14}$ | 85% | 88% |
| UF1 Product | 185.7 | $1.58 \times 10^{12}$ | $2.93 \times 10^{14}$ | 87% | 77% |
| AE Product | 101.6 | $1.76 \times 10^{12}$ | $1.79 \times 10^{14}$ | 63% | 48% |
| UF2 Product | 135.9 | $1.13 \times 10^{12}$ | $1.54 \times 10^{14}$ | 92% | 44% |
| Sterile-Filtered Product | 141.4 | $1.01 \times 10^{12}$ | $1.43 \times 10^{14}$ | 100% | 44% |

[1]Filtered through 0.45 micron PVDF syringe filter prior to assay
[2]Results calculated from Ad5 standard curve
[3]Step yields consider sampling of intermediates (not shown).

TABLE 15

Impurity Clearance During 20-L Scale Ad6 Purification

| Sample | DNA (QPCR) pg/$10^{11}$ vp | Protein (BCA), ug/$10^{11}$ vp | Triton % | DB % |
|---|---|---|---|---|
| Lysate | 5.8E+06 | 641 | 0.135 | — |
| Clarified Lysate | 4.2E+04 | 439 | 0.084 | 0.016 |
| UF1 Product | 310 | 37 | 0.017 | 0.041 |
| AE Product | 20 | 10 | <0.0012 | <0.0008 |
| UF2 Product | 5 | 10 | <0.0012 | <0.0008 |
| Sterile-Filtered Product | 3 | 7 | <0.0012 | <0.0008 |

EXAMPLE 11

Adenovirus Type 35 (Ad35pol)

In this example, adenovirus type 35 (from subgroup B) is purified. Process changes as compared to Example 5 were predominantly in the preparative anion exchange chromatography step. There, the UF1 product was diluted to approximately 28 mS/cm and loaded on to the Source 15Q resin. The column was washed with 0.29 M NaCl and eluted in a four column volume gradient to 0.38 M NaCl. Otherwise, the process was run essentially as described in Examples 5 and 9.

Yields from this purification demonstrate that process performance is comparable to Ad5 (Table 16). Specific residual DNA levels by Q-PCR were reduced by over 3 logs following precipitation and clarification to 11 ng/$10^{11}$ vp. Levels are reduced to 1.0 ng/$10^{11}$ vp following the first ultrafiltration (UF1). Specific total protein values (Table 17) also indicate that the vast majority of the total protein is removed by the end of UF1; these data indicate that this product reaches relatively high purity without any chromatographic purification and that many subgroups of adenovirus may be purified by the existing process, namely subjecting a clarified, SPA-precipitated lysate to a single ultrafiltration step.

TABLE 16

Ad35 Yield Table For 20-L Scale Purification

| Sample | Vol, mL | AEX, vp/mL[2] | Ad, vp | Step Yield[2] | Net Yield |
|---|---|---|---|---|---|
| Lysate | 20723 | $4.31 \times 10^{10}$ | $8.93 \times 10^{14}$ | — | — |
| Precipitate[1] | 22371 | $3.64 \times 10^{10}$ | $8.14 \times 10^{14}$ | 91% | 91% |
| Clarified Lysate | 22259 | $2.86 \times 10^{10}$ | $6.37 \times 10^{14}$ | 78% | 71% |
| UF1 Product | 949 | $4.54 \times 10^{11}$ | $4.31 \times 10^{14}$ | 75% | 53% |
| AE Product | 137 | $2.85 \times 10^{12}$ | $3.91 \times 10^{14}$ | 93% | 49% |
| UF2 Product | 448 | $6.64 \times 10^{11}$ | $2.97 \times 10^{14}$ | 78% | 39% |
| Sterile-Filtered Product | 438 | $6.43 \times 10^{11}$ | $2.81 \times 10^{14}$ | 99% | 38% |

[1]Filtered through 0.45 micron PVDF syringe filter prior to assay
[2]Results calculated from Ad5 standard curve
[3]Step yields consider sampling of intermediates (not shown).

TABLE 17

Protein Clearance During Ad35 20-L Purification

| Sample | Protein (BCA), ug/$10^{11}$ vp |
|---|---|
| Lysate | 1803 |
| Clarified Lysate | 1549 |
| UF1 Product | 24 |
| AE Product | 17 |
| UF2 Product | 14 |
| Sterile-Filtered Product | 15 |

EXAMPLE 12

Separation of Adenovirus Types 5, 24 and 36 by Anion Exchange

Figure 9:
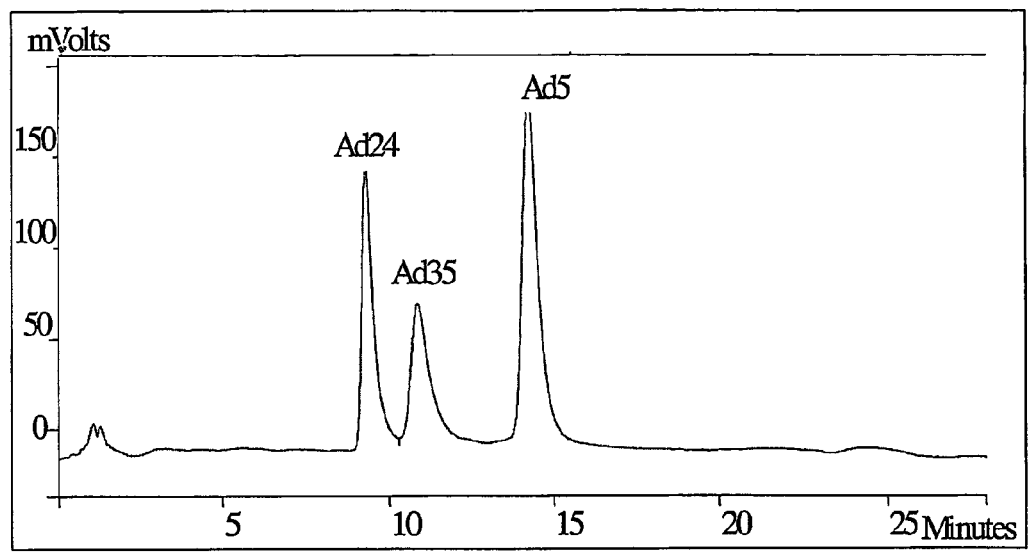
FIG. 9 shows separation times for various recombinant adenovirus serotypes (Ad5, Ad24 and Ad35) by anion exchange chromatography.

Small quantities of chromatography or CsCl-ultracentrifugation-purified adenovirus were injected on an analytical scale Source 15Q column (see FIG. 9). In this example, a NaCl gradient of 0.2 to 0.6 M was used. The method clearly is able to bind/elute virus from subgroup C (Ad5), subgroup D (Ad24), or subgroup B (Ad35). In addition, by injecting new types with a known type (in this case Ad5), the relative elution time can be calculated; from the relative elution time and knowledge of preparative buffers for Ad5, preparative buffers for any other serotype can easily be determined. This change is the only notable modification necessary to adapt this invention to other adenovirus serotypes.

EXAMPLE 13

Domiphen Bromide Precipitation of Adenovirus Types 5, 35 and 6

A range of DB concentrations (0 to 0.065%) were added to 1 mL vials of different adenovirus cell lysates containing approximately 0.1% Triton, 0.05% PS-80, 2 mM $MgCl_2$, and 25 mM Tris, pH 8. Cells were prepared in suspension culture with infection at roughly $10^6$ cells/mL. These samples were immediately vortexed and filtered with 0.45 micron syringe filters. Aliquots were removed for the determination of adenovirus and DNA concentrations via AEX-HPLC and Picogreen assays.

Figure 10:
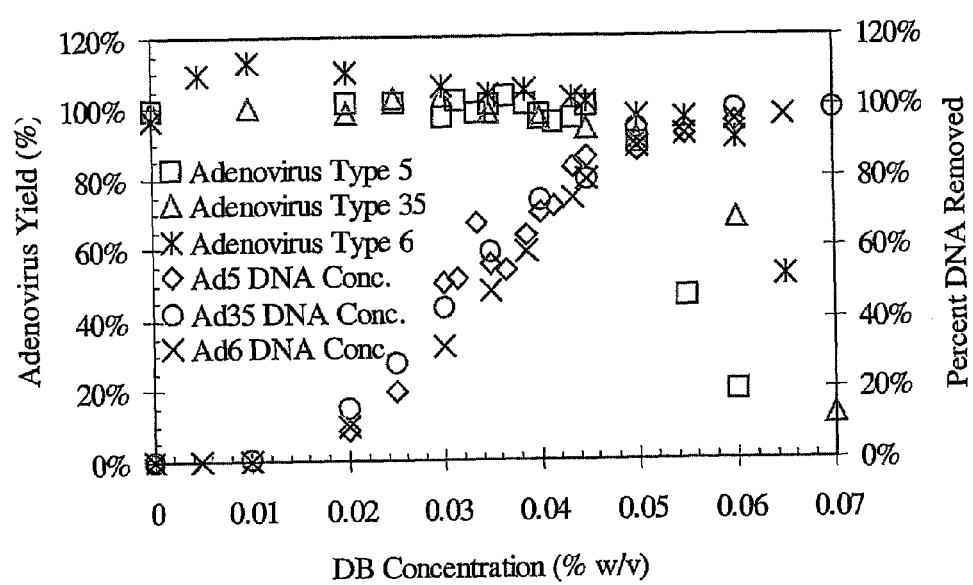
FIG. 10 shows the concentration effect of domiphen bromide on various serotypes of recombinant adenovirus and DNA from each respective recombinant virus.

As shown in FIG. 10, adenovirus does not measurably precipitate at concentrations of domiphen bromide below 0.05%. Therefore, addition of domiphen bromide at levels between 0.03 and 0.05% will result in selective precipitation of DNA. For the particular stream properties used here, addition at 0.04% is suitable for all serotypes. Precipitation of residual impurities by CPC, CTAB, and alternative SPAs mentioned also shows similar performance across multiple adenovirus subgroups.

EXAMPLE 14

Ad5 Purification Process with Cation Exchange

The purification of adenovirus using a process including cation exchange may proceed through anion exchange chromatography as described in prior examples. This example describes the processing of the anion exchange product through a second ultrafiltration, a pH adjustment, flow-through cation exchange, and a second pH/buffer adjustment to arrive at a product in a final formulation buffer.

The anion exchange product was diluted and adjusted to an adenovirus concentration of approximately $1.77 \times 10^{12}$ vp/mL and a salt concentration of 1 M NaCl. The batch was diafiltered into buffer (5 mM Tris, 10 mM NaCl, 1 mM $MgCl_2$, 5% sucrose, 0.005% PS-80, pH 7.4) via three 0.05 $m^2$ 300 kDa PES membranes (Millipore Pellicon XL). The permeate flux was maintained at 80 mL/min-$m^2$.

The ultrafiltered retentate was pH adjusted to about 6.5 with buffer (5 mM Tris, 0.2 M Histidine, 10 mM NaCl, 1 mM $MgCl_2$, 5% sucrose, 0.005% PS-80, 50 mM HCl, pH 6.5) prior to the cation exchange chromatography step. A 1.6 cm diameter Vantage L column (Millipore Corporation) was packed with 18.8 mL of Source 30S resin (Amersham Biosciences). The product was loaded at a linear velocity of 1 cm/min and washed with 6 column volumes of buffer (5 mM Tris, 10 mM Histidine, 10 mM NaCl, 1 mM $MgCl_2$, 5% sucrose, 0.02% PS-80, pH 6.5). The operation was run in flow-through mode and product collection stopped once the $A_{260}$ approached baseline level. The product was adjusted to formulation conditions by adding 0.17 M Tris, 10 mM Histidine, 2.27 M NaCl, 1 mM $MgCl_2$, 5% sucrose, 0.02% PS-80, pH 9.3 buffer. Table 18 shows the yield for this process.

TABLE 18

MRKAd5gag Yield Table for Ultrafiltration and Cation Exchange

| Sample | Vol, mL | AEX, vp/mL | Ad, vp | Step Yield* | Net Yield |
|---|---|---|---|---|---|
| AEP | 80.6 | 3.96E12 | 3.19E14 | — | — |
| UF2 feed | 179.5 | 1.77E12 | 3.17E14 | 99% | 99% |
| UF2 retentate | 206.9 | 1.26E12 | 2.61E14 | 83% | 83% |
| Pre-CEX adjustment | 199.1 | 1.18E12 | 2.35E14 | 97% | 80% |
| CEP | 224.2 | 8.55E11 | 1.92E14 | 88% | 71% |
| Post-CEX adjustment | 223.0 | 8.49E11 | 1.89E14 | 102% | 72% |

*Step yields account for sampling between steps (not shown).

EXAMPLE 15

Clarification of Precipitated Lysate with Continuous Centrifugation-MRK Ad5pol

This example demonstrates that a continuous centrifuge with a polishing depth filter can be used to clarify the precipitated cell lysate. Precipitated cell lysate from an Ad5 lot was centrifuged using a CARR Pilot Powerfuge continuous centrifuge at a 2 min residence time and both 20,000 G and 10,000 G. The bowl used had a volume of approximately 1 L. The centrate was fed continuously into a CUNO CP50 depth filter at 0.14 LPM/$ft^2$ at a loading of 60 L/$ft^2$. Timepoint centrate and filtrate samples were taken periodically to monitor the clarification progress. Adenovirus yields across the centrifugation were in excess of 90%, with an overall clarification yield of 80%. The turbidity of the clarified lysate was less than 2 NTU. The pooled clarified lysate was then processed forward as described in other examples with similar results in terms of residual DNA clearance, protein purity, and product infectivity.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A method of purifying adenovirus particles from a cell culture medium comprising adenovirus particles which comprises:
   a) lysing host cells within the cell culture medium;
   b) selectively precipitating impurity DNA away from the adenovirus particles by adding a selective precipitation agent to the cell culture medium, wherein the selective precipitation agent is selected from the group consisting of domiphen bromide (DB), cetylpyridinium chloride (CPC), cetyltrimethylammonium bromide (CTAB), benzethonium chloride (BTC), tetradecyltrimethylammonium bromide or chloride (TTA), and polyethylene imine (PEI);
   c) clarifying the cell culture medium; and
   d) recovering purified adenovirus particles from the cell culture medium;
wherein at least 80% of impurity DNA is precipitated away from the cell culture medium.

2. The method of claim 1 which further comprises:
   e) conducting ultrafiltration on the adenovirus-containing medium recovered from step d); and
   f) recovering concentrated, purified adenovirus particles.

3. The method of claim 1 wherein step d) is performed by a method selected from the group consisting of depth filtration, dead end filtration, microfiltration, centrifugation or a combination thereof.

4. The method of claim 1 wherein step d) is performed by depth filtration.

5. The method of claim 1 wherein step d) is performed by the combination of centrifugation and depth filtration.

6. The method of claim 2 wherein the purified adenovirus particles recovered from step f) are subjected to cation exchange chromatography.

7. The method of claim 1 wherein the clarified medium recovered from step d) is treated with a nuclease.

8. The method of claim 1 which further comprises:
   e) subjecting the adenovirus-containing medium recovered from step d) to anion exchange chromatography;
   f) diafiltering the adenovirus-containing eluate recovered from step e); and
   g) recovering concentrated, purified adenovirus.

9. The method of claim 8 wherein step d) is performed by a method selected from the group consisting of depth filtration, dead end filtration, microfiltration, centrifugation or a combination thereof.

10. The method of claim 1 which further comprises:
    e) conducting a first ultrafiltration process on the adenovirus-containing medium recovered from step d);
    f) subjecting the adenovirus-containing medium recovered from step e) to anion exchange chromatography;
    g) conducting a second ultrafiltration process on the adenovirus-containing medium recovered from step f);
    h) optionally subjecting the adenovirus particles recovered from step g) to cation exchange chromatography; and
    i) recovering concentrated, purified adenovirus.

11. The method of claim 10 wherein step d) is performed by a method selected from the group consisting of depth filtration, dead end filtration, microfiltration, centrifugation or a combination thereof.

12. The method of claim 10 wherein step d) is performed by depth filtration.

13. The method of claim 10 wherein step d) is performed by the combination of centrifugation and depth filtration.

14. The method of claim 1 which further comprises subjecting medium comprising the purified adenovirus particles to anion exchange chromatography wherein said anion exchange chromatography employs a buffer comprising a detergent.

15. The method of claim 14 wherein the detergent is a non-ionic surfactant.

16. The method of claim 15 wherein the detergent is polysorbate-80 (PS-80).

17. The method of claim 16 wherein the concentration of PS-80 is 0.1%.

18. The method of claim 1 which further comprises a diafiltration step into a buffer with a pH between 6.5 and 8.0.

19. The method of claim 18 wherein diafiltration is into a buffer comprising 50 mM HEPES, 2 mM MgCl2, 1 M NaCl, pH7.5.

20. The method of claim 18 wherein the buffer further comprises polysorbate-80 (PS-80).

* * * * *